United States Patent
Tsai et al.

(10) Patent No.: US 9,101,326 B2
(45) Date of Patent: Aug. 11, 2015

(54) METHOD AND SYSTEM OF IMAGE RECONSTRUCTION AND METHOD AND SYSTEM OF IMAGE CONSTRUCTION

(71) Applicant: Industrial Technology Research Institute, Hsinchu (TW)

(72) Inventors: Meng-Han Tsai, Hsinchu County (TW); Jheng-You Lin, Taichung (TW); Hsin-Han Shen, Taoyuan County (TW); Guo-Zua Wu, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 4 days.

(21) Appl. No.: 13/914,648

(22) Filed: Jun. 11, 2013

(65) Prior Publication Data

US 2014/0105479 A1    Apr. 17, 2014

Related U.S. Application Data

(60) Provisional application No. 61/712,281, filed on Oct. 11, 2012.

(30) Foreign Application Priority Data

Feb. 19, 2013  (TW) .............................. 102105746 A

(51) Int. Cl.
| | | |
|---|---|---|
| A61B 6/00 | (2006.01) | |
| G06T 7/00 | (2006.01) | |
| A61B 6/06 | (2006.01) | |

(52) U.S. Cl.
CPC ... *A61B 6/52* (2013.01); *A61B 6/06* (2013.01); *A61B 6/4241* (2013.01); *A61B 6/4429* (2013.01); *A61B 6/482* (2013.01); *G06T 7/0012* (2013.01)

(58) Field of Classification Search
CPC ....... A61B 6/482; G01N 23/06; G01V 5/0041
See application file for complete search history.

(56) References Cited

U.S. PATENT DOCUMENTS

| 7,668,289 B2 | 2/2010 | Proksa et al. |
|---|---|---|
| 7,813,470 B2 | 10/2010 | Kuwabara |

(Continued)

FOREIGN PATENT DOCUMENTS

| CN | 101166968 | 4/2008 |
|---|---|---|
| CN | 101405597 | 4/2009 |

(Continued)

OTHER PUBLICATIONS

Xiaolan Wang, et al., "Material separation in x-ray CT with energy resolved photon-counting detectors", Medical Physics, vol. 38, No. 3, Mar. 2011, pp. 1534-1546.

(Continued)

*Primary Examiner* — Amir Alavi
*Assistant Examiner* — Kenny Cese
(74) *Attorney, Agent, or Firm* — Jianq Chyun IP Office

(57) ABSTRACT

A method of image reconstruction is provided. When an object is not placed in a measurement space, first intensity images of an electromagnetic wave passing through the measurement space and corresponding to photon energy levels are measured. When the object is placed in the measurement space, second intensity images of the electromagnetic wave passing through the object and corresponding to photon energy levels are measured. In a database, data including an attenuation coefficient of each substance respectively having components irradiated by the electromagnetic wave corresponding to each photon energy level and a thickness of each substance in a transmission direction of the electromagnetic wave corresponding to each photon energy level are provided. Attenuation images of the object respectively corresponding to the components are calculated according to the data and the first and second intensity images. An image reconstruction system and a method and system of image construction are also provided.

15 Claims, 7 Drawing Sheets

(56) References Cited

U.S. PATENT DOCUMENTS

| | | |
|---|---|---|
| 8,213,566 B2 | 7/2012 | Roessl et al. |
| 2008/0118023 A1 | 5/2008 | Besson |
| 2009/0052621 A1 | 2/2009 | Walter et al. |
| 2010/0027867 A1* | 2/2010 | Bernhardt et al. ............ 382/132 |
| 2011/0096892 A1 | 4/2011 | Forthmann et al. |
| 2011/0164797 A1 | 7/2011 | Jang et al. |

FOREIGN PATENT DOCUMENTS

| | | |
|---|---|---|
| CN | 101416073 | 4/2009 |
| CN | 102076263 | 5/2011 |
| CN | 102088907 | 6/2011 |
| CN | 102196773 | 9/2011 |
| CN | 102413767 | 4/2012 |
| CN | 102573634 | 7/2012 |
| CN | 102711612 | 10/2012 |
| JP | 09-134434 | 5/1997 |
| TW | 200801571 | 1/2008 |
| TW | 201238564 | 10/2012 |

OTHER PUBLICATIONS

X Wang, et al., "MicroCT with energy-resolved photon-counting detectors", Phys Med Biol., vol. 56, No. 9, May 7, 2011, pp. 2791-2816.

Hyo-Min Cho, et al., "The Effects of Spectral Distortion on Multi-Energy X-ray Imaging Based on Photon Counting Detector", IEEE, Nuclear Science Symposium and Medical Imaging Conference (NSS/MIC), Oct. 23-29, 2011, pp. 3001-3003.

Jiyoung Choi, et al., "A Statistical Framework for Material Decomposition Using Multi-Energy Photon Counting X-Ray Detector", IEEE, 9th IEEE International Symposium on Biomedical Imaging (ISBI), May 2-5, 2012, pp. 1300-1303.

Xiaolan Wang, et al., "A Digital Line-Camera for Energy Resolved X-ray Photon Counting", IEEE, Nuclear Science Symposium Conference Record, Oct. 24, 2009-Nov. 1, 2009, pp. 3453-3457.

Shih-Hsiu Wang, "Investigation of attenuation correction for micro PET," Master Thesis, Institute of Radiological Sciences, National Yang-Ming University, Aug. 2006.

"Office Action of Taiwan Counterpart Application," issued on Feb. 10, 2015, p. 1-p. 5.

"Office Action of Chinese Counterpart Application", issued on Apr. 15, 2015, p.1-p.5.

\* cited by examiner

METHOD AND SYSTEM OF IMAGE RECONSTRUCTION AND METHOD AND SYSTEM OF IMAGE CONSTRUCTION

CROSS-REFERENCE TO RELATED APPLICATION

This application claims the priority benefits of U.S. provisional application Ser. No. 61/712,281, filed on Oct. 11, 2012, and Taiwan application serial no. 102105746, filed on Feb. 19, 2013. The entirety of each of the above-mentioned patent applications is hereby incorporated by reference herein and made a part of this specification.

BACKGROUND

1. Technical Field

The disclosure relates to a method and a system of image reconstruction as well as a method and a system of image construction.

2. Related Art

In accordance with the medical researches on risk factors for cancers, e.g., for breast cancer, the strongest known risk factor is high breast density (breast composition). The breast density may be categorized into six levels: 0, <10% (less than 10% glandular tissue), 10% to 25%, 25% to 50%, 50% to 75%, and >75%. The denser the breast, the more likely to develop breast cancer.

Imaging on patients (including human beings and animals), e.g., taking photographs of body regions where malignant lesions may occur, help a doctor diagnose cancer. For instance, a doctor may evaluate and determine whether a woman has breast cancer through mammography. According to statistical results, ductal carcinoma in situ (DCIS) of the breast cancer discovered by mammography accounts for approximately 20% of all kinds of breast cancers, and 90% of the stage-0 DCIS of the breast cancer is diagnosed through micro-calcifications. Calcifications are often scattered throughout the mammary glands. In the breast with high density, the calcifications and the mammary glands are indicative of high X-ray absorption and are frequently overlapped. Hence, the calcifications may not be easily distinguished from the mammary glands through the two-dimensional X-ray images obtained by applying the existing mammography, which may mislead the diagnosis of the doctor.

To precisely observe the internal conditions of patients, a computed tomography (CT) scan technique may be applied. For instance, the CT scan technique may be performed to learn the internal structure of human breasts. According to the CT scan, plural two-dimensional X-ray images of the breast are taken in various directions. A three-dimensional image is then generated from the two-dimensional X-ray images through computer simulation. Although the CT scan allows the doctor to learn the internal conditions of human breasts in an accurate manner, the high radiation in form of X-rays used for taking the two-dimensional X-ray images in the CT scan process may lead to high possibility of cancer.

SUMMARY

In an exemplary embodiment of the disclosure, a method of image reconstruction is provided for reconstructing an image of an object. The method includes following steps. When the object is not placed in a measurement space, a plurality of first intensity images of an electromagnetic wave passing through the measurement space and respectively corresponding to a plurality of photon energy levels are measured. When the object is placed in the measurement space, a plurality of second intensity images of the electromagnetic wave passing through the object and respectively corresponding to the photon energy levels are measured. Data in a database are provided. The data include an attenuation coefficient of each of a plurality of substances respectively having a plurality of components irradiated by the electromagnetic wave corresponding to each of the photon energy levels and a thickness of each of the substances in a transmission direction of the electromagnetic wave corresponding to the photon energy level. According to the data in the database, the first intensity images, and the second intensity images, a plurality of attenuation images of the object respectively corresponding to the components are calculated.

In an exemplary embodiment of the disclosure, a system of image reconstruction is provided for reconstructing an image of an object. The system includes an electromagnetic wave providing unit, an electromagnetic wave detector, and a processing unit. The electromagnetic wave providing unit provides an electromagnetic wave. The electromagnetic wave detector measures a plurality of first intensity images of the electromagnetic wave passing through a measurement space and corresponding to a plurality of photon energy levels when the object is not placed in the measurement space. Besides, the electromagnetic wave detector measures a plurality of second intensity images of the electromagnetic wave passing through the object and corresponding to the photon energy levels when the object is placed in the measurement space. Data in a database include an attenuation coefficient of each of a plurality of substances respectively having a plurality of components irradiated by the electromagnetic wave corresponding to each of the photon energy levels and a thickness of each of the substances in a transmission direction of the electromagnetic wave corresponding to the photon energy level. The processing unit calculates a plurality of attenuation images of the object respectively corresponding to the components according to the data in the database, the first intensity images, and the second intensity images.

In an exemplary embodiment of the disclosure, a method of image construction is provided for constructing an image of an object. The method includes following steps. A pulsed electromagnetic wave beam is provided. A plurality of blocks of the object is scanned by the pulsed electromagnetic wave beam. When intensity of the pulsed electromagnetic wave beam is substantially zero, an alignment position of the pulsed electromagnetic wave beam is relatively moved from one of the blocks to another of the blocks; when the intensity of the pulsed electromagnetic wave beam is substantially not zero, the alignment of the pulsed electromagnetic wave beam is kept still with respect to the object. When the alignment position of the pulsed electromagnetic wave beam respectively rests at the blocks, a plurality of intensities of the pulsed electromagnetic wave beam having passed through the blocks are respectively measured. A correspondence relation between the intensities of the pulsed electromagnetic wave beam having passed through the blocks and the blocks is recorded. The image of the object is constructed according to the intensities of the pulsed electromagnetic wave beam having passed through the blocks and the correspondence relation.

In an exemplary embodiment of the disclosure, a system of image construction is provided for constructing an image of an object. The system includes a pulsed electromagnetic wave beam providing unit, a control unit, an electromagnetic wave detector, and a processing unit. The pulsed electromagnetic wave beam providing unit includes a pulsed electromagnetic wave source and a collimator. The pulsed electromagnetic wave source provides a pulsed electromagnetic wave. The collimator is disposed on a transmission path of the pulsed electromagnetic wave. Besides, the collimator has a hole. A portion of the pulsed electromagnetic wave passes through the hole of the collimator to form a pulsed electromagnetic wave beam. The control unit causes the pulsed electromagnetic wave beam to scan a plurality of blocks of the object by moving the collimator. When intensity of the pulsed electromagnetic wave beam is substantially zero, the control unit relatively moves an alignment position of the pulsed electromagnetic wave beam from one of the blocks to another of the blocks. When the intensity of the pulsed electromagnetic wave beam is substantially not zero, the control unit causes the alignment position of the pulsed electromagnetic wave beam to be kept still with respect to the object. When the alignment position of the pulsed electromagnetic wave beam rests at the blocks, respectively, the electromagnetic wave detector measures the intensities of the pulsed electromagnetic wave beam having passed through the blocks. The processing unit records a correspondence relation between the intensities of the pulsed electromagnetic wave beam having passed through the blocks and the blocks and constructs the image of the object according to the intensities of the pulsed electromagnetic wave beam having passed through the blocks and the correspondence relation.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

First Exemplary Embodiment

Figure 1:
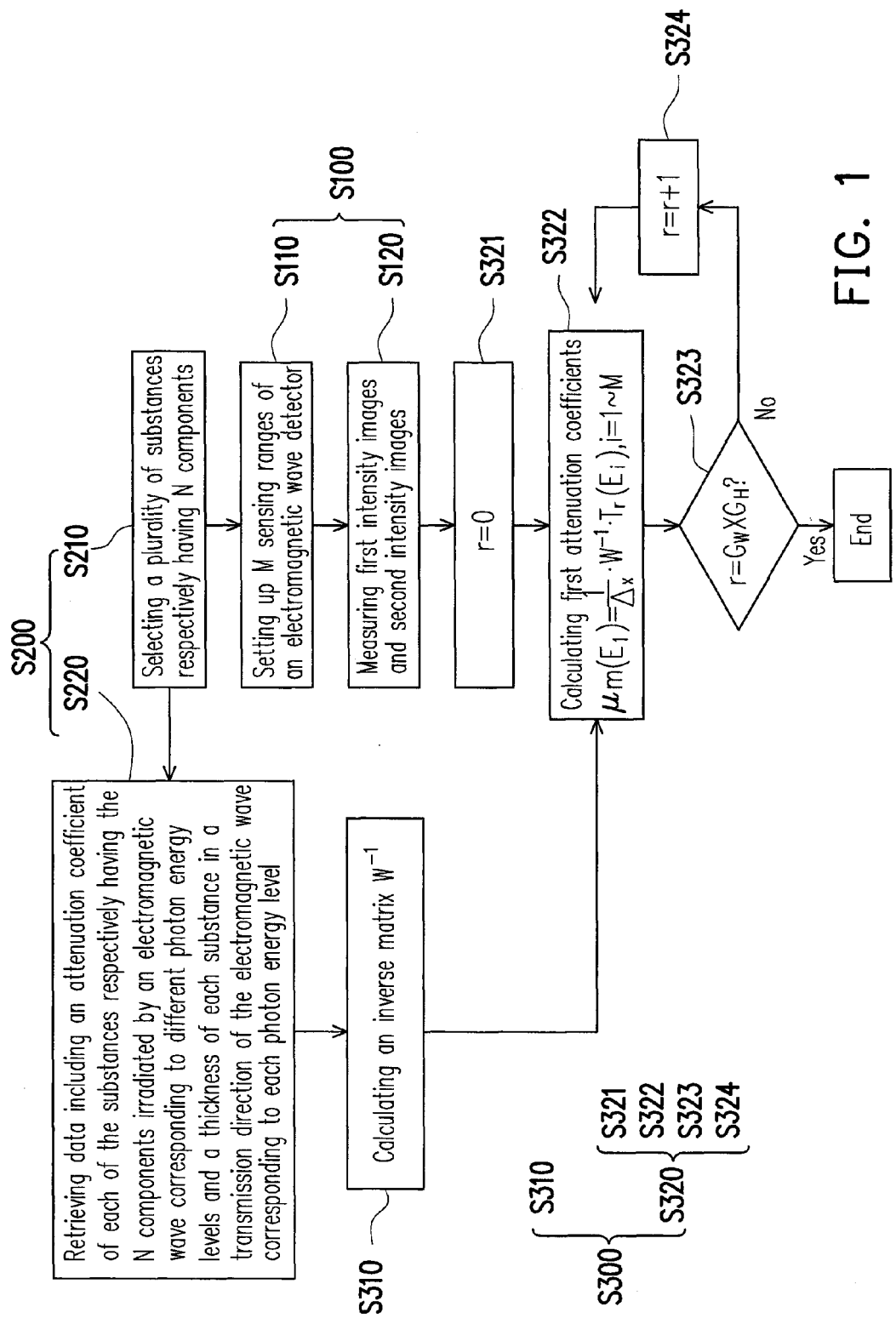
FIG. 1 is a flow chart illustrating a method of image reconstruction according to a first exemplary embodiment of the disclosure.

FIG. 1 is a flow chart illustrating a method of image reconstruction according to a first exemplary embodiment of the disclosure. In the present exemplary embodiment, the method of image reconstruction is provided for reconstructing an image of an object. The object described herein is a human breast, for instance. However, the disclosure is not limited thereto, and the object in other embodiments of the disclosure may be parts of or all of the body of a living organism (including human beings, animals, and plants) or a non-living object.

With reference to FIG. 1, the method of image reconstruction described in the present exemplary embodiment includes steps S100, S200, and S300. Note that the order of performing the steps S100, S200, and S300 may be appropriately adjusted. For instance, the steps S200, S100, and S300 may be sequentially performed. The method and the system of image reconstruction are elaborated hereinafter with reference to FIG. 1 and FIG. 2.

Figure 2:
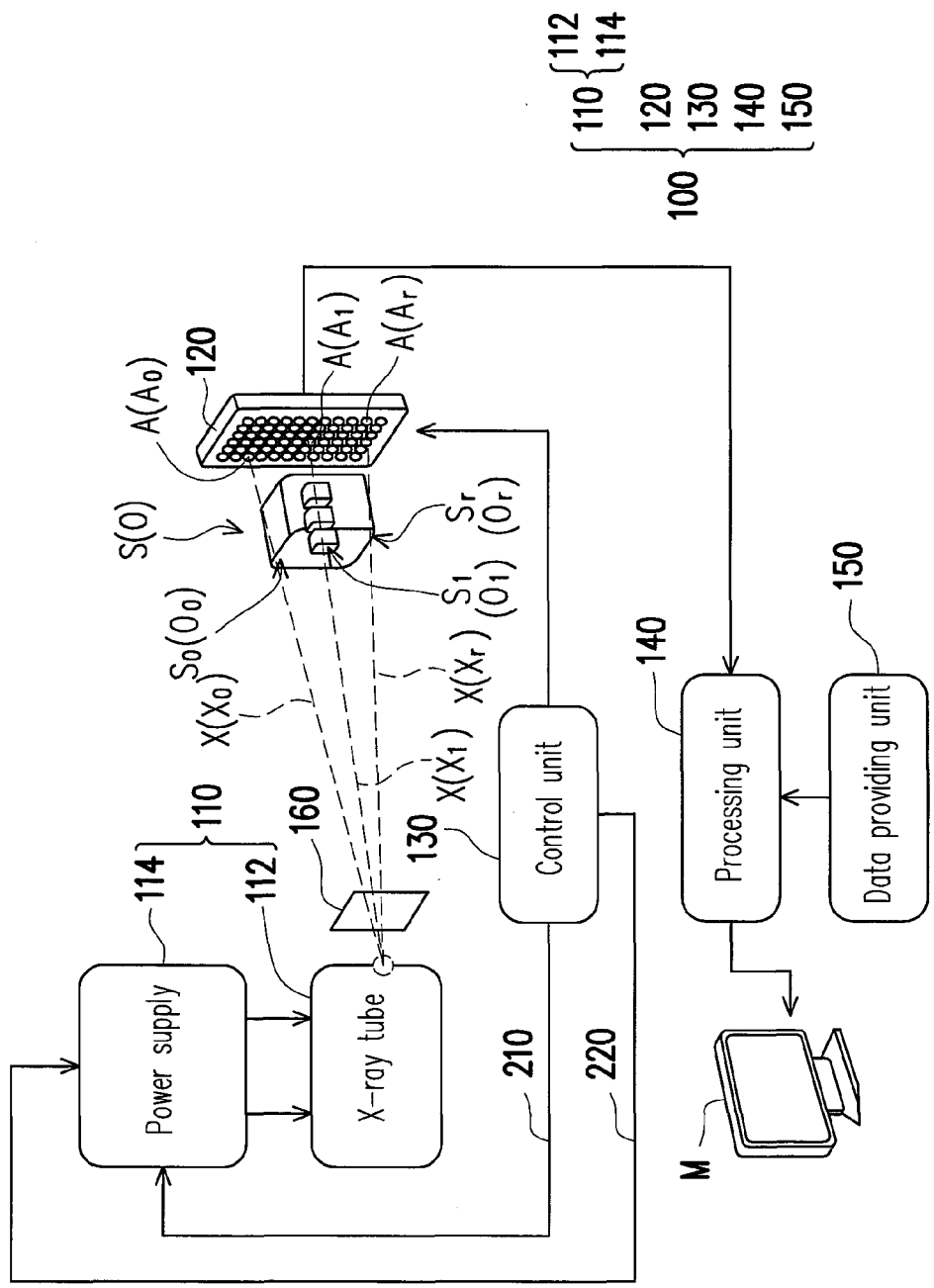
FIG. 2 illustrates a system of image reconstruction according to the first exemplary embodiment of the disclosure.

As shown in FIG. 1 and FIG. 2, data in a database are provided. The data in the database include an attenuation coefficient of each of a plurality of substances respectively having a plurality of components irradiated by an electromagnetic wave corresponding to each of a plurality of photon energy levels and a thickness of each of the substances in a transmission direction of the electromagnetic wave corresponding to each of the photon energy levels (step S200). In detail, the step of providing the data in the database includes following sub-steps. N components respectively corresponding to a plurality of attenuation images of an object O may be determined, and thereby the substances having the N components may be selected in step S210. Here, N is a positive integer greater than zero. In step S220, the data including the attenuation coefficient of each of the substances having the N components irradiated by the electromagnetic wave corresponding to each of the photon energy levels and the thickness of each of the substances in a transmission direction of the electromagnetic wave corresponding to each of the photon energy levels are then retrieved from the database. For instance, given that the object is the breast, and when the three attenuation images of the breast corresponding to fat, mammary gland, and calcifications (i.e., the cancer lesions) are to be obtained, the data including the attenuation coefficient of each of the fat, the mammary gland, and the calcifications irradiated by the electromagnetic wave corresponding to at least three different photon energy levels and the thickness of each of the fat, the mammary gland, and the calcifications in the transmission direction of the electromagnetic wave corresponding to the different photon energy levels may be retrieved from the database.

Specifically, the system 100 of image reconstruction described herein may alternatively include a data providing unit 150. The data providing unit 150 may provide the aforesaid data in the database. According to the N components respectively corresponding to the attenuation images of the object O, the system 100 of image reconstruction may obtain the attenuation coefficient of each of the substances respectively having the N components irradiated by the electromagnetic wave corresponding to different photon energy levels and the thickness of each of the substances in the transmission direction of the electromagnetic wave corresponding to each of the different photon energy levels through the data providing unit 150. In the present exemplary embodiment, the data providing unit 150 may be a network unit capable of downloading the attenuation coefficient of each of the substances respectively having a plurality of components irradiated by the electromagnetic wave corresponding to each of the photon energy levels and the thickness of each of the substances in the transmission direction of the electromagnetic wave corresponding to the photon energy level from the network.

However, the disclosure is not limited thereto; in another exemplary embodiment of the disclosure, the data providing unit 150 may be a storage unit capable of storing the attenuation coefficient of each of the substances respectively having a plurality of components irradiated by the electromagnetic wave corresponding to each of the photon energy levels and the thickness of each of the substances in the transmission direction of the electromagnetic wave corresponding to each of the photon energy levels. In still another exemplary embodiment of the disclosure, the data providing unit 150 may be an input interface for a user to input the attenuation coefficient of each of the substances respectively having a plurality of components irradiated by the electromagnetic wave corresponding to each of the photon energy levels and the thickness of each of the substances in the transmission direction of the electromagnetic wave corresponding to each of the photon energy levels.

When the object O is not placed in a measurement space S, a plurality of first intensity images of the electromagnetic wave X passing through the measurement space S and corresponding to a plurality of photon energy levels are measured; when the object O is placed in the measurement space S, a plurality of second intensity images of the electromagnetic wave X passing through the object O and corresponding to the photon energy levels are measured (step S100). Specifically, the system 100 of image reconstruction described herein includes an electromagnetic wave detector 120. The electromagnetic wave detector 120 in step S110 may set up M sensing ranges before measuring the first intensity images and the second intensity images. Here, M is a positive integer greater than or equal to N; that is, the number of the sensing ranges set by the electromagnetic wave detector 120 may be greater than or equal to the number of the attenuation images corresponding to a plurality of components of the object O. When the object O is not placed in the measurement space S, the first intensity images of the electromagnetic wave X passing through the measurement space S and corresponding to M different photon energy levels are measured; when the object O is placed in the measurement space S, the second intensity images of the electromagnetic wave X passing through the object O and corresponding to the M photon energy levels are measured (step S120).

In particular, as shown in FIG. 2, the object O may be divided into a plurality of blocks $O_0, O_1, \ldots,$ and $O_r$, and the measurement space S may be divided into a plurality of measurement sub-spaces $S_0, S_1, \ldots,$ and $S_r$. The blocks $O_0, O_1, \ldots,$ and $O_r$ are predetermined to be placed in the measurement sub-spaces $S_0, S_1, \ldots,$ and $S_r$. In the present exemplary embodiment, the system 100 of image reconstruction includes an electromagnetic wave providing unit 110. The electromagnetic wave providing unit 110 provides an electromagnetic wave X. Here, the electromagnetic wave X includes a plurality of electromagnetic wave beams $X_0, X_1, \ldots,$ and $X_r$ that respectively pass through the corresponding measurement sub-spaces $S_0, S_1, \ldots,$ and $S_r$. The step of measuring the first intensity images of the electromagnetic wave X passing through the measurement space S and corresponding to the different photon energy levels includes: measuring a plurality of first intensities of the electromagnetic wave beams $X_0, X_1, \ldots$ and $X_r$ respectively passing through the measurement sub-spaces $S_0, S_1, \ldots,$ and $S_r$ and corresponding to the photon energy levels when the blocks $O_0, O_1, \ldots,$ and $O_r$ are not placed in the measurement sub-spaces $S_0, S_1, \ldots,$ and $S_r$. Here, the first intensities of the electromagnetic wave beams $X_0, X_1, \ldots$ and $X_r$ passing through the measurement sub-spaces $S_0, S_1, \ldots,$ and $S_r$ and corresponding to the photon energy levels respectively constitute the first intensity images. When the object O is placed in the measurement space S, the step of measuring the second intensity images of the electromagnetic wave X passing through the object O and corresponding to the photon energy levels includes: measuring a plurality of second intensities of the electromagnetic wave beams $X_0, X_1, \ldots,$ and $X_r$ respectively passing through the blocks $O_0, O_1, \ldots,$ and $O_r$ and corresponding to the photon energy levels when the blocks $O_0, O_1, \ldots,$ and $O_r$ are placed in the measurement sub-spaces $S_0, S_1, \ldots,$ and $S_r$. Here, the second intensities of the electromagnetic wave beams $X_0, X_1, \ldots,$ and $X_r$ passing through the blocks $O_0, O_1, \ldots,$ and $O_r$ and corresponding to the photon energy levels respectively constitute the second intensity images.

In the present exemplary embodiment, the electromagnetic wave beams $X_0, X_1, \ldots,$ and $X_r$ may simultaneously pass through the measurement sub-spaces $S_0, S_1, \ldots,$ and $S_r$, and the first intensities of the electromagnetic wave beams $X_0, X_1, \ldots,$ and $X_r$ passing through the measurement sub-spaces $S_0, S_1, \ldots,$ and $S_r$ and corresponding to the photon energy levels are simultaneously measured. The electromagnetic wave beams $X_0, X_1, \ldots,$ and $X_r$ may simultaneously pass through the blocks $O_0, O_1, \ldots,$ and $O_r$, and the second intensities of the electromagnetic wave beams $X_0, X_1, \ldots,$ and $X_r$ passing through the blocks $O_0, O_1, \ldots,$ and $O_r$ and corresponding to the photon energy levels are simultaneously measured.

Particularly, as shown in FIG. 2, the electromagnetic wave providing unit 110 provides the electromagnetic wave X, and the electromagnetic wave X includes a plurality of electromagnetic wave beams $X_0, X_1, \ldots,$ and $X_r$. As described in the present exemplary embodiment, the electromagnetic wave detector 120 has a plurality of sensing pixels A corresponding to the measurement sub-spaces $S_0, S_1, \ldots,$ and $S_r$, and the electromagnetic wave providing unit 110 may simultaneously emit a plurality of electromagnetic wave beams $X_0, X_1, \ldots,$ and $X_r$. The sensing pixels A of the electromagnetic wave detector 120 may simultaneously measure a plurality of first intensities of the electromagnetic wave beams $X_0, X_1, \ldots,$ and $X_r$ respectively passing through the measurement sub-spaces $S_0, S_1, \ldots,$ and $S_r$ and corresponding to the photon energy levels. Besides, the sensing pixels A of the electromagnetic wave detector 120 may simultaneously measure a plurality of second intensities of the electromagnetic wave beams $X_0, X_1, \ldots,$ and $X_r$ respectively passing through the blocks $O_0, O_1, \ldots,$ and $O_r$ and corresponding to the photon energy levels.

Figures 3, 4:
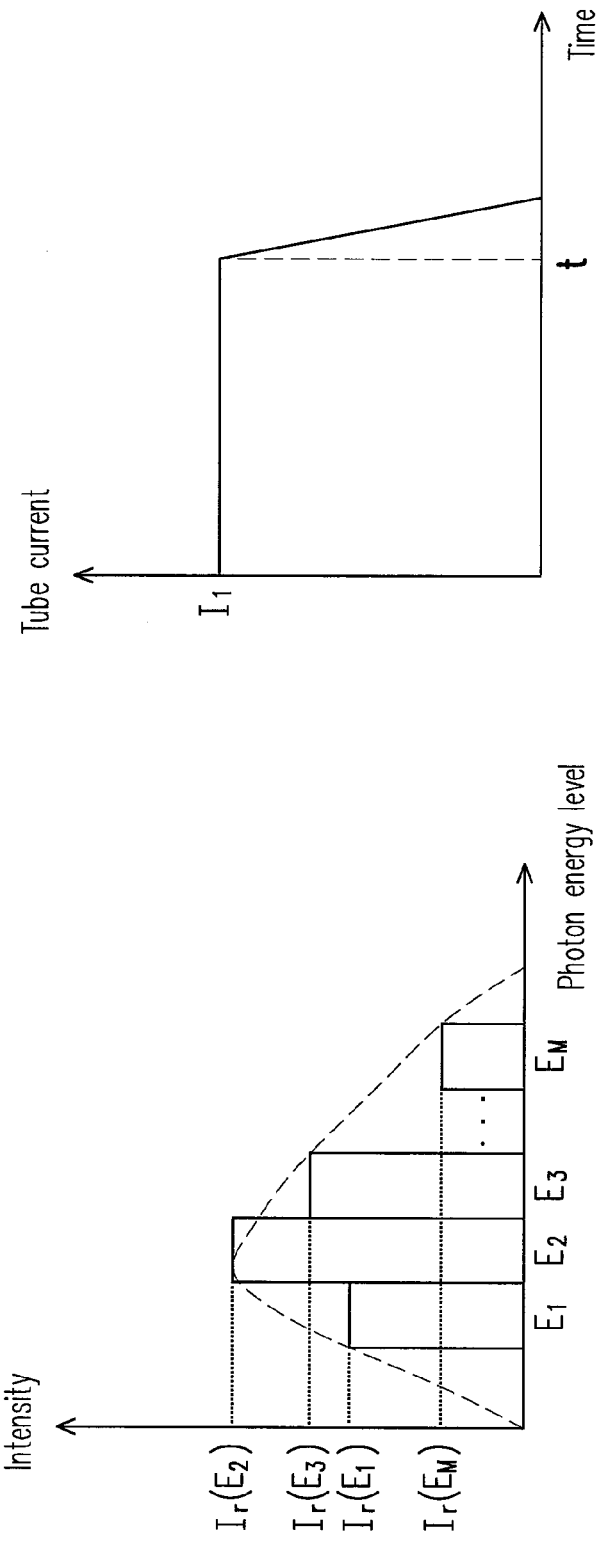
FIG. 3 illustrates a plurality of intensities of an electromagnetic wave beam measured by a sensing pixel according to an exemplary embodiment of the disclosure, and the electromagnetic wave beam corresponds to a plurality of photon energy levels.
FIG. 4 illustrates a relationship between time and a tube current flowing through an X-ray tube according to an exemplary embodiment of the disclosure.

According to the present exemplary embodiment, the electromagnetic wave detector 120 is a photon-counting detector, for instance, and each of the sensing pixels A of the electromagnetic wave detector 120 may individually measure a plurality of intensities of the electromagnetic wave beams $X_0, X_1, \ldots,$ and $X_r$ which are respectively transmitted to the sensing pixel A and correspond to the photon energy levels. FIG. 3 illustrates a plurality of intensities of an electromagnetic wave beam measured by a sensing pixel according to an exemplary embodiment of the disclosure, and the electromagnetic wave beam corresponds to a plurality of photon energy levels. With reference to FIG. 3, specifically, each of the sensing pixels A may sense the number of photons in the electromagnetic wave beam $X_r$ that is transmitted to the sensing pixel A and corresponds to the photon energy levels $E_1, E_2, \ldots,$ and $E_M$. Based on the number of the photons, it is likely to learn the intensities $I_r(E_1), I_r(E_2), \ldots,$ and $I_r(E_M)$ of the electromagnetic wave beam $X_r$ that is transmitted to the sensing pixel A and corresponds to the photon energy levels $E_1, E_2, \ldots,$ and $E_M$.

In the present exemplary embodiment, the electromagnetic wave providing unit 110 may be operated in a continuous mode. That is, during the measuring period of the electromagnetic wave detector 120 (i.e., during the period of measuring the first intensities and the second intensities), the intensities of the electromagnetic wave beams $X_0, X_1, \ldots,$ and $X_r$ emitted by the electromagnetic wave providing unit 110 may have constant values. Particularly, as shown in FIG. 2, the system 100 of image reconstruction described in the present exemplary embodiment may further include a control unit 130 that is electrically connected to the electromagnetic wave providing unit 110 and the electromagnetic wave detector 120. The control unit 130 causes the intensities of the electromagnetic wave beams $X_0, X_1, \ldots,$ and $X_r$ emitted by the electromagnetic wave providing unit 110 to have constant values during the measuring period of the electromagnetic wave detector 120. For instance, the electromagnetic wave providing unit 110 serves to provide an X-ray. The X-ray providing unit may include an X-ray tube 112 and a power supply 114 electrically connected to the X-ray tube 112. The control unit 130 may respectively control the voltage and the current input from the power supply 114 to the X-ray tube 112 through transmission channels 210 and 220 and thereby control the X-ray tube 112 to be operated in a continuous mode.

FIG. 4 illustrates a relationship between time and a tube current flowing through an X-ray tube according to an exemplary embodiment of the disclosure. With reference to FIG. 4, when the X-ray tube 112 is operated in the continuous mode, the tube current flowing through the X-ray tube 112 has the constant value (i.e., the fixed current $I_1$) during the measuring period t of the electromagnetic wave detector 120, and thereby the intensities of the electromagnetic wave beams (i.e., the X-ray beams) output by the X-ray tube 112 are constant during the measuring period t.

With reference to FIG. 1 and FIG. 2, after the first intensity images, the second intensity images, the attenuation coefficients of a plurality of substances respectively having a plurality of components irradiated by the electromagnetic wave corresponding to each of the photon energy levels, and the thicknesses of the substances in a transmission direction of the electromagnetic wave corresponding to the photon energy levels are obtained, a plurality of attenuation images of the object respectively corresponding to the components may be calculated according to the first intensity images, the second intensity images, the required attenuation coefficients, and the required thicknesses (step S300). Namely, a plurality of first attenuation coefficients of each of the blocks respectively corresponding to each of the components irradiated by the electromagnetic wave beam corresponding to each of the photon energy levels may be calculated according to the first intensities of the electromagnetic wave beams $X_0, X_1, \ldots,$ and $X_r$ respectively passing through the measurement subspaces $S_0, S_1, \ldots,$ and $S_r$ and corresponding to the photon energy levels, the second intensities of the electromagnetic wave beams $X_0, X_1, \ldots,$ and $X_r$ respectively passing through the blocks $O_0, O_1, \ldots,$ and $O_r$ and corresponding to the photon energy levels, the attenuation coefficients of the substances respectively having a plurality of components irradiated by the electromagnetic wave corresponding to each of the photon energy levels, and the thicknesses of the substances. Here, the first attenuation coefficients of each block constitute the aforesaid attenuation images.

The following exemplary embodiment is provided to describe the method of calculating the first attenuation coefficients of a certain block corresponding to the components irradiated by the electromagnetic wave corresponding to a certain photon energy level (e.g., the first photon energy level $E_1$).

With reference to FIG. 1, according to the attenuation coefficients of the substances, conversion relations between the attenuation coefficient of each component irradiated by the electromagnetic wave beam corresponding to each photon energy level and the attenuation coefficients of such a component irradiated by the electromagnetic wave beams corresponding to the other photon energy levels are calculated, and an inverse matrix $W^{-1}$ of a conversion matrix W is established according to the conversion relations (step S310). For instance, the components include a first component, a second component to an $N^{th}$ component, and N is a positive integer greater than or equal to 2. The photon energy levels include a first photon energy level $E_1$, a second photon energy level $E_2$ to an $M^{th}$ photon energy level $E_M$, and M is a positive integer greater than or equal to N. According to the attenuation coefficients of the substances, the conversion relations $w(\mu_{r1}, E_2)$ to $w(\mu_{r1}, E_M)$ between the attenuation coefficient $\mu_{r1}(E_1)$ of the first component irradiated by the electromagnetic wave beam $X_r$ corresponding to the first photon energy level $E_1$ and the attenuation coefficients $\mu_{r1}(E_2)$ to $\mu_{r1}(E_M)$ of the first component irradiated by the electromagnetic wave beam $X_r$ corresponding to the second photon energy level $E_2$ to the $M^{th}$ photon energy level $E_M$ are calculated. For instance, the conversion relations $w(\mu_{r1}, E_2)$ to $w(\mu_{r1}, E_M)$ are represented as $w(\mu_{r1}, E_2) = [\mu_{r1}(E_2)/\mu_{r1}(E_1)]$, $w(\mu_{r1}, E_3) = [\mu_{r1}(E_3)/\mu_{r1}(E_1)] \ldots$, and $w(\mu_{r1}, E_M) = [\mu_{r1}(E_M)/\mu_{r1}(E_1)]$. Similarly, according to the attenuation coefficients, the conversion relations $w(\mu_{r2}, E_2)$ to $w(\mu_{r2}, E_M)$ between the attenuation coefficient $\mu_{r2}(E_1)$ of the second component irradiated by the electromagnetic wave beam $X_r$ corresponding to the first photon energy level $E_1$ and the attenuation coefficients $\mu_{r2}(E_2)$ to $\mu_{r2}(E_M)$ of the second component irradiated by the electromagnetic wave beam $X_r$ corresponding to the second photon energy level $E_2$ to the $M^{th}$ photon energy level $E_M$ to the conversion relations $w(\mu_{rN}, E_2)$ to $w(\mu_{rN}, E_M)$ between the attenuation coefficient $\mu_{rN}(E_1)$ of the $N^{th}$ component irradiated by the electromagnetic wave beam $X_r$ corresponding to the first photon energy level $E_1$ and the attenuation coefficients $\mu_{rN}(E_2)$ to $\mu_{rN}(E_M)$ of the $N^{th}$ component irradiated by the electromagnetic wave beam $X_r$ corresponding to the second photon energy level $E_2$ to the $M^{th}$ photon energy level $E_M$ are calculated. The conversion matrix W may be established according to the conversion relations. The conversion matrix W may be represented as the following equation (1), and thereby the inverse matrix $W^{-1}$ of the conversion matrix W may be calculated.

$$W = \begin{bmatrix} 1 & 1 & \ldots & 1 \\ w(\mu_{r1}, E_2) & w(\mu_{r2}, E_2) & \ldots & w(\mu_{rN}, E_2) \\ \vdots & \vdots & \ddots & \vdots \\ w(\mu_{r1}, E_M) & w(\mu_{r2}, E_M) & \ldots & w(\mu_{rN}, E_M) \end{bmatrix}. \quad (1)$$

With reference to FIG. 1, a proportion matrix is then established according to the first intensities of the electromagnetic wave beam passing through each of the measurement subspaces and corresponding to the photon energy levels and the second intensities of the electromagnetic wave beam passing through each of the blocks and corresponding to the photon energy levels, and the first attenuation coefficients of each of the blocks respectively corresponding to the components irradiated by the electromagnetic wave corresponding to each photon energy level are calculated according to the proportion matrix, the conversion matrix W, and the thicknesses of the substances (step S320).

The following exemplary embodiment is provided to describe the method of calculating the first attenuation coefficients of a certain block $O_r$ corresponding to the components irradiated by the electromagnetic wave beam corresponding to the first photon energy level $E_1$ (step 322). A proportion matrix $T_r$ is established according to the first intensities of the electromagnetic wave beam $X_r$ passing through the measurement sub-space $S_r$ and corresponding to the M photon energy levels and the second intensities of the electromagnetic wave beam $X_r$ passing through the block $O_r$ and corresponding to the M photon energy levels. To be specific, the first intensities of the electromagnetic wave beam passing through each of the measurement sub-spaces and corresponding to the first photon energy level $E_1$, the second photon energy level $E_2$ to the $M^{th}$ photon energy level $E_M$ are respectively represented as $I_{r1}(E_1)$, $I_{r1}(E_2)$ to $I_{r1}(E_M)$, the second intensities of the electromagnetic wave beam passing through each of the blocks and corresponding to the first photon energy level $E_1$, the second photon energy level $E_2$ to the $M^{th}$ photon energy level $E_M$ are respectively represented as $I_{r2}(E_1)$, $I_{r2}(E_2)$, to $I_{r2}(E_M)$, and the proportion matrix $T_r$ is represented as the following equation (2):

$$T_r = \begin{bmatrix} -\ln\left(\frac{I_{r2}(E_1)}{I_{r1}(E_1)}\right) \\ -\ln\left(\frac{I_{r2}(E_2)}{I_{r1}(E_2)}\right) \\ \vdots \\ -\ln\left(\frac{I_{r2}(E_M)}{I_{r1}(E_M)}\right) \end{bmatrix}. \quad (2)$$

According to the proportion matrix $T_r$ and the conversion matrix W, the first attenuation coefficients of the block $O_r$ corresponding to the first, second to $N^{th}$ components irradiated by the electromagnetic wave beam corresponding to the first photon energy level $E_1$ are calculated. Specifically, the first attenuation coefficients $\mu_{r1}(E_1)$, $\mu_{r2}(E_1)$ to $\mu_{rN}(E_1)$ of the block $O_r$ corresponding to the first, second to $N^{th}$ components irradiated by the electromagnetic wave beam corresponding to the first photon energy level $E_1$ may be calculated by the following equation (3):

$$\begin{bmatrix} \mu_{r1}(E_1) \cdot t_1 \\ \mu_{r2}(E_1) \cdot t_2 \\ \vdots \\ \mu_{rN}(E_1) \cdot t_N \end{bmatrix} = W^{-1} \cdot T_r. \quad (3)$$

Here, $t_1$, $t_2$ to $t_N$ respectively represent the thickness of the substance having the first component and transmitted in the transmission direction of the electromagnetic wave beam corresponding to the photon energy level, the thickness of the substance having the second component and transmitted in the transmission direction of the electromagnetic wave beam corresponding to the photon energy level to the thickness of the substance having the $N^{th}$ component and transmitted in the transmission direction of the electromagnetic wave beam corresponding to the photon energy level. In the present exemplary embodiment, the thicknesses $t_1$, $t_2$ to $t_N$ may be the distance $\Delta x$ between two plates (not shown) which clamp the object O (e.g., the breast). However, in other exemplary embodiments of the disclosure, the thicknesses $t_1$, $t_2$ to $t_N$ may be obtained from statistical data and thus should not be construed as a limitation to the disclosure. If the thicknesses $t_1$, $t_2$ to $t_N$ refer to the distance $\Delta x$, the equation (3) may be simplified to be the following equation (4):

$$\begin{bmatrix} \mu_{r1}(E_1) \\ \mu_{r2}(E_1) \\ \vdots \\ \mu_{rN}(E_1) \end{bmatrix} = \frac{1}{\Delta x} \cdot W^{-1} \cdot T_r. \quad (4)$$

The equation (4) is $$\mu_{ri}(E_1) = \frac{1}{\Delta x} \cdot W^{-1} \cdot T_r(E_i), \; i = 1 \sim M$$

as listed in FIG. 1.

The aforementioned exemplary embodiment is provided to describe the method of calculating the first attenuation coefficients $\mu_{r1}(E_1)$, $\mu_{r2}(E_1)$ to $\mu_{rN}(E_1)$ of a certain block $O_r$ corresponding to the components irradiated by the electromagnetic wave beam corresponding to the first photon energy level $E_1$. Similarly, the first attenuation coefficients $\mu_{r1}(E_2)$ to $\mu_{rN}(E_2)$, to $\mu_{r1}(E_M)$ to $\mu_{rN}(E_M)$ of the block $O_r$ corresponding to the components irradiated by the electromagnetic wave beams corresponding to the other photon energy levels may also be calculated. In addition, after the first attenuation coefficients $\mu_{r1}(E_1)$ to $\mu_{rN}(E_1)$, $\mu_{r1}(E_2)$ to $\mu_{rN}(E_2)$, ..., and $\mu_{r1}(E_M)$ to $\mu_{rN}(E_M)$ are respectively stored, a user is able to select the first attenuation coefficients corresponding to certain photon energy level and thereby observe the attenuation of the block corresponding to each component. The attenuations of other blocks corresponding to each component may be reconstructed by applying the similar method. After the attenuations of all the blocks corresponding to all of the components are calculated, the attenuations of all the blocks corresponding to each component irradiated by the electromagnetic wave beam corresponding to one single photon energy level may be obtained. The following explanations are provided with reference to FIG. 1 and FIG. 2.

As shown in FIG. 1 and FIG. 2, the electromagnetic wave detector 120 described in the present exemplary embodiment includes a plurality of sensing pixels A, and each of the sensing pixels A corresponds to one of the measurement sub-spaces (as well as the block in the measurement sub-space). The sensing pixels A are arranged in a ($G_H \cdot G_W$) array. That is, the electromagnetic wave detector 120 described in the present exemplary embodiment includes ($G_H \cdot G_W$) sensing pixels A. Here, the first intensities and the second intensities sensed by the first sensing pixel $A_0$ corresponding to the first measurement sub-space ($S_r$, r=0) and the first block ($O_r$, =0) may be obtained in step S321. According to the first and second intensities, the first attenuation coefficients of the first block corresponding to the components irradiated by the electromagnetic wave beam corresponding to the first photon energy level $E_1$ are calculated (step 322). It is then determined whether the obtained sensing pixel A is the ($G_H \cdot G_W$)$^{th}$ sensing pixel A, i.e., the last sensing pixel A. That is, in step S323, whether r is equal to ($G_H \cdot G_W$) is determined. If r is not equal to (GH·GW), 1 is added to the value of r (step S324), so as to obtain the first intensities and the second intensities sensed by the next sensing pixel $A_1$ corresponding to the next measurement sub-space ($S_r$, r=1) and the next block ($O_r$, r=1).

According to the first and second intensities, the first attenuation coefficients of the next block ($O_r$, r=1) corresponding to the components irradiated by the electromagnetic wave beam corresponding to the first photon energy level $E_1$ are calculated (step 322). The steps S323, S324, and S322 are cyclically performed. Once r is equal to ($G_H \cdot G_W$), i.e., the first attenuation coefficients of all blocks corresponding to the components irradiated by the electromagnetic wave beam corresponding to the first photon energy level $E_1$ are completely calculated, the calculation is terminated.

The above-mentioned exemplary embodiment is provided to describe the method of calculating the first attenuation coefficients of a certain block corresponding to the components irradiated by the electromagnetic wave corresponding to a certain photon energy level (e.g., the first photon energy level $E_1$). Similarly, the first attenuation coefficients of the block corresponding to the components irradiated by the electromagnetic wave beams corresponding to the other photon energy levels may also be calculated. The attenuation of each block of the object corresponding to a certain component constitutes the attenuation image of the object having the component irradiated by the electromagnetic wave corresponding to a certain photon energy level.

With reference to FIG. 2, the system 100 of image reconstruction described herein includes a processing unit 140 capable of performing said steps S200 and S300; since the steps performed by the processing unit 140 may be referred to as the steps S200 and S300 explained above, no further description in this regard is further provided. Besides, the system 100 of image reconstruction described herein may further display the attenuation images (which are calculated by the processing unit 140 and correspond to the components) on a screen M.

In the present exemplary embodiment, before the electromagnetic wave beams $X_0$, $X_1$, ..., and $X_r$ are caused to simultaneously pass through the measurement sub-spaces $S_0$, $S_1$, ..., and $S_r$ and the blocks $O_0$, $O_1$, ..., and $O_r$, part of the electromagnetic wave beams $X_0$, $X_1$, ..., and $X_r$ having photon energy less than a minimum of the photon energy levels may be filtered out. Specifically, as shown in FIG. 2, the system 100 of image reconstruction described herein may further include a filter unit 160. The filter unit 160 is disposed on a transmission path of the electromagnetic wave beams $X_0$, $X_1$, ..., and $X_r$ and located between the electromagnetic wave providing unit 110 and the measurement sub-spaces $S_0$, $S_1$, ..., and $S_r$. Here, the filter unit 160 serves to filter out part of the electromagnetic wave beams $X_0$, $X_1$, ..., and $X_r$ having photon energy less than a minimum photon energy level $E_1$ of the photon energy levels $E_1$, $E_2$ to $E_M$. That is, the filter unit 160 is able to filter out unnecessary part of the electromagnetic wave X, such that the object O may absorb less amount of energy. Provided that the object O is the human breast and the electromagnetic wave X is the X-ray, the filter unit 160 may reduce the radiation absorbed by the human body and thereby alleviate damages to the human body during the radiographic examination.

In view of the above, according to the method and the system of image reconstruction described herein, the attenuation images of the object having the components may be calculated by applying the aforesaid data processing method, and each component of the object may respectively constitute an attenuation image. As such, each component of the object may be clearly observed. Besides, in the method and the system of image reconstruction, the attenuation images of the object having the components may be obtained by performing a one-time image obtaining process on the object (i.e., obtaining the second intensity images in one step), such that the object does not absorb excessive amount of radiation, and that the resultant damages to the object during the radiographic examination may be mitigated.

Second Exemplary Embodiment

The method and the system of image reconstruction described herein are similar to those provided in the first exemplary embodiment, and thus the same steps and the same components are represented by the same reference numbers. The main difference between the two exemplary embodiments lies in the method of obtaining the first intensity images and the second intensity images, which will be elaborated hereinafter. By contrast, the similarities between the method and the system of image reconstruction described herein and those provided in the first exemplary embodiment will not be further explained.

Figure 5:
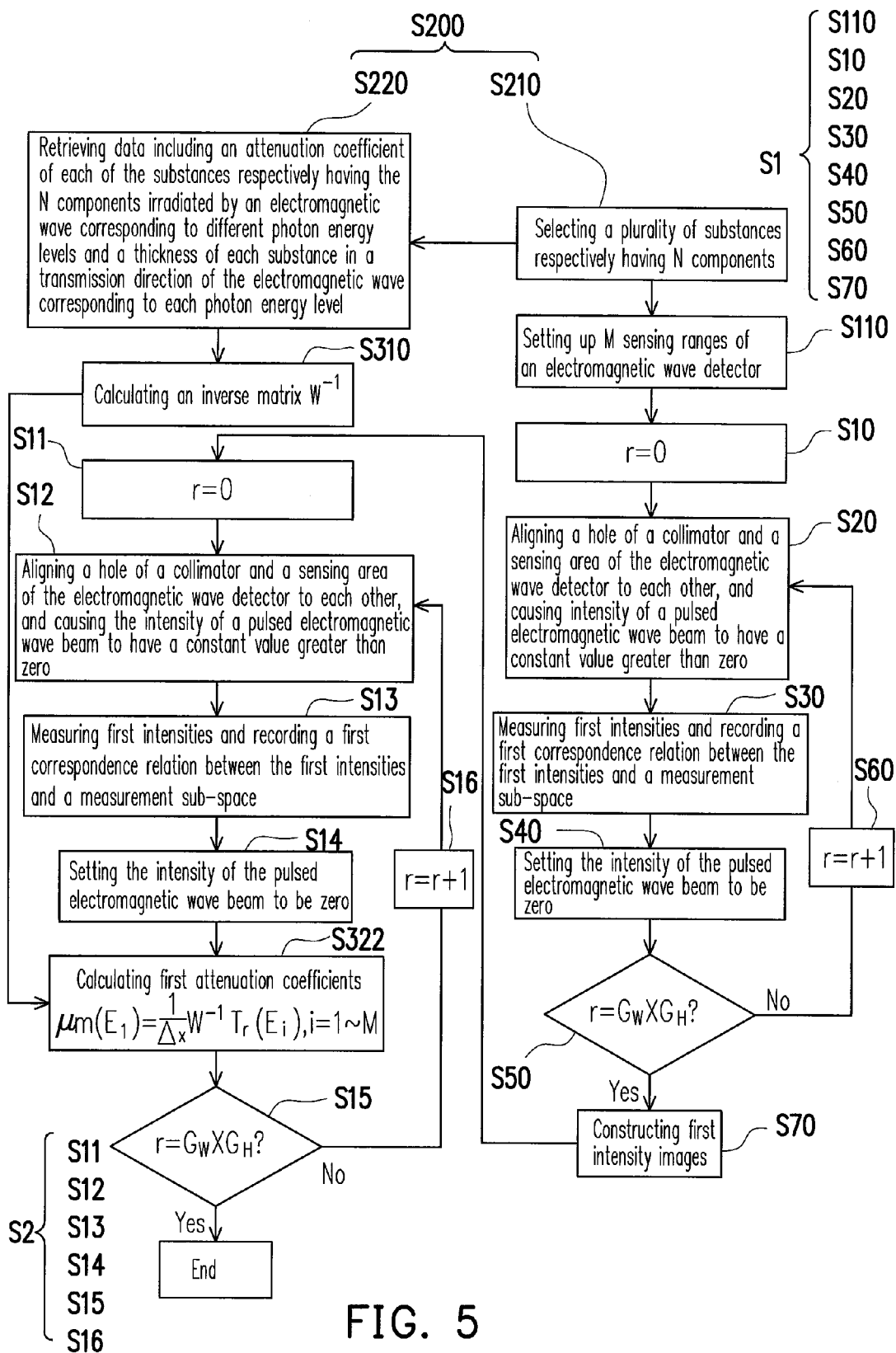
FIG. 5 is a flow chart illustrating a method of image reconstruction according to a second exemplary embodiment of the disclosure.
Figure 6:
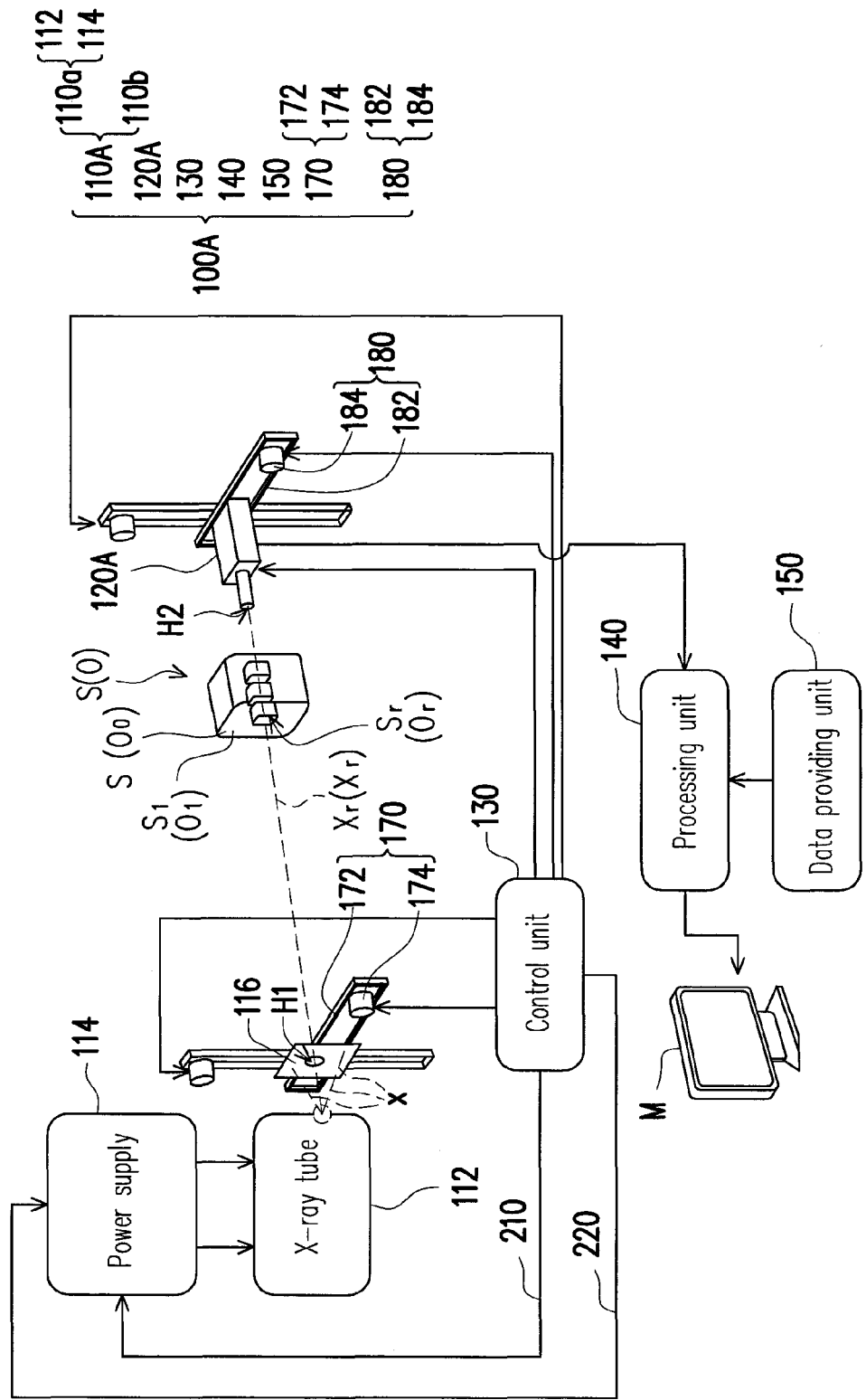
FIG. 6 illustrates a system of image reconstruction according to the second exemplary embodiment of the disclosure.

FIG. 5 is a flow chart illustrating a method of image reconstruction according to a second exemplary embodiment of the disclosure. FIG. 6 illustrates a system of image reconstruction according to the second exemplary embodiment of the disclosure. Note that the method of image reconstruction shown in FIG. 5 is applicable to the system of image reconstruction depicted in FIG. 6. With reference to FIG. 5, data in a database are provided. The data in the database include an attenuation coefficient of each of a plurality of substances respectively having a plurality of components irradiated by an electromagnetic wave corresponding to each of a plurality of photon energy levels and a thickness of each of the substances in a transmission direction of the electromagnetic wave corresponding to each of the photon energy levels (step S200). In detail, the step of providing the data in the database includes following sub-steps. N components respectively corresponding to a plurality of attenuation images of an object O may be determined, and thereby the substances having the N components may be selected in step S210. In step S220, the data including the attenuation coefficient of each of the substances having the N components irradiated by the electromagnetic wave corresponding to each of the photon energy levels and the thickness of each of the substances in a transmission direction of the electromagnetic wave corresponding to each of the photon energy levels are then retrieved from the database.

With reference to FIG. 6, specifically, the system 100A of image reconstruction described herein may alternatively include a data providing unit 150. In the present exemplary embodiment, the system 100A of image reconstruction further includes a processing unit 140. According to the N components respectively corresponding to the attenuation images of the object O, the processing unit 140 of the system 100A of image reconstruction may obtain the attenuation coefficient of each of the substances respectively having the N components irradiated by the electromagnetic wave corresponding to different photon energy levels and the thickness of each of the substances in the transmission direction of the electromagnetic wave corresponding to each of the different photon energy levels.

With reference to FIG. 5, according to the attenuation coefficients of the substances, conversion relations between the attenuation coefficient of each component irradiated by the electromagnetic wave beam corresponding to each photon energy level and the attenuation coefficients of such a component irradiated by the electromagnetic wave beams corresponding to the other photon energy levels are calculated, and an inverse matrix $W^{-1}$ of a conversion matrix W is established according to the conversion relations (step S310). With reference to FIG. 6, according to the attenuation coefficients of the substances, the processing unit 140 described in the present exemplary embodiment may calculate conversion relations between the attenuation coefficient of each component irradiated by the electromagnetic wave beam corresponding to each photon energy level and the attenuation coefficients of such a component irradiated by the electromagnetic wave beams corresponding to the other photon energy levels and establish an inverse matrix $W^{-1}$ of a conversion matrix W according to the conversion relations. The detailed steps of calculating the conversion relations and establishing the inverse matrix $W^{-1}$ may be referred to as those provided in the first exemplary embodiment.

As shown in FIG. 5 and FIG. 6, when the object O is not placed in the measurement space S, the first intensity images of the electromagnetic wave passing through the measurement space S and corresponding to the photon energy levels $E_1, E_2, \ldots,$ and $E_M$ are measured (step S1). Namely, when the blocks $O_0, O_1, \ldots,$ and $O_r$ are not placed in the measurement sub-spaces $S_0, S_1, \ldots,$ and $S_r$, the first intensities $I_{r1}(E_1)$, $I_{r1}(E_2)$ to $I_{r1}(E_M)$ of the electromagnetic wave passing through each of the measurement sub-spaces $S_0, S_1, \ldots,$ and $S_r$ and corresponding to the photon energy levels $E_1, E_2, \ldots,$ and $E_M$ are measured (step S1).

Different from the first exemplary embodiment, the present exemplary embodiment discloses that the electromagnetic wave beam $X_r$ may be a pulsed electromagnetic wave beam $x_r$. The step of measuring the first intensities $I_{r1}(E_1), I_{r1}(E_2)$ to $I_{r1}(E_M)$ of the electromagnetic wave beam $X_r$ passing through the measurement sub-space $S_r$ and corresponding to the photon energy levels $E_1, E_2, \ldots,$ and $E_M$ includes: causing the pulsed electromagnetic wave beam $x_r$ to scan the measurement sub-spaces $S_0, S_1, \ldots,$ and $S_r$, wherein when intensity of the pulsed electromagnetic wave beam $x_r$ is substantially zero, the alignment position of the pulsed electromagnetic wave beam $x_r$ is relatively moved from one of the measurement sub-spaces to another of the measurement sub-spaces. When the intensity of the pulsed electromagnetic wave beam $x_r$ is substantially not zero, the alignment position of the pulsed electromagnetic wave beam $x_r$ is kept substantially still with respect to one of the measurement sub-spaces. When the alignment position of the pulsed electromagnetic wave beam $x_r$ respectively rests at the measurement sub-spaces $S_0, S_1, \ldots,$ and $S_r$, the first intensities $I_{r1}(E_1), I_{r1}(E_2)$ to $I_{r1}(E_M)$ of the pulsed electromagnetic wave beam $x_r$ passing through the measurement sub-space $S_r$ and corresponding to the photon energy levels $E_1, E_2, \ldots,$ and $E_M$ are respectively measured.

With reference to FIG. 6, specifically, the system 100A of image reconstruction described herein may alternatively include an electromagnetic wave providing unit 110A that provides pulsed electromagnetic wave beams. According to the present exemplary embodiment, the electromagnetic wave providing unit 110A is a pulsed electromagnetic wave providing unit, and the pulsed electromagnetic wave providing unit includes a pulsed electromagnetic wave source 110a that provides the pulsed electromagnetic wave x and a collimator 116. The pulsed electromagnetic wave source 110a includes an X-ray tube 112 and a power supply 114. In the present exemplary embodiment, the system 100A of image reconstruction may further include a control unit 130 that is electrically connected to the electromagnetic wave providing unit 110A. The control unit 130 may respectively control the voltage and the current input from the power supply 114 to the X-ray tube 112 through transmission channels 210 and 220 and thereby control the X-ray tube 112 to emit the pulsed electromagnetic wave x.

The collimator 116 described herein is disposed on a transmission path of the pulsed electromagnetic wave x. Besides, the collimator 116 has a hole H1. A portion of the pulsed electromagnetic wave x passes through the hole H1 of the collimator 116 to form the pulsed electromagnetic wave beam $x_r$. The control unit 130 causes the pulsed electromagnetic wave beam $x_r$ to scan the measurement sub-spaces $S_0, S_1, \ldots,$ and $S_r$ by moving the collimator 116. When the intensity of the pulsed electromagnetic wave beam $x_r$ is substantially zero, the control unit 130 causes an alignment position of the pulsed electromagnetic wave beam $x_r$ to be moved from one of the measurement sub-spaces $S_0, S_1, \ldots,$ and $S_r$ to another of the measurement sub-spaces $S_0, S_1, \ldots,$ and $S_r$. When the intensity of the pulsed electromagnetic wave beam $x_r$ is substantially not zero (e.g., when the intensity has a constant value), the control unit 130 controls the alignment position of the pulsed electromagnetic wave beam $x_r$ to be kept still with respect to the one of the measurement sub-spaces, and the electromagnetic wave detector 120A of the system 100A of image reconstruction respectively measures the first intensities of the pulsed electromagnetic wave beam $x_r$ passing through each of the measurement sub-spaces $S_0, S_1, \ldots,$ and $S_r$ when the alignment position of the pulsed electromagnetic wave beam $x_r$ respectively rests at the measurement sub-spaces.

As shown in FIG. 5 and FIG. 6, when the object O is not placed in the measurement space S, the method of measuring the first intensity images of the electromagnetic wave passing through the measurement space S and corresponding to the photon energy levels $E_1, E_2, \ldots,$ and $E_M$ includes steps S110, S10, S20, S30, S40, S50, S60, and S70, which will be elaborated hereinafter. The electromagnetic wave detector 120 in step S110 may set up M sensing ranges, so as to subsequently measure the first intensity images (and the second intensity images) of the electromagnetic wave corresponding to M different photon energy levels, and M is a positive integer greater than or equal to N. According to the present exemplary embodiment, the electromagnetic wave detector 120 may be a photon-counting spectrometer, for instance, which should however not be construed as a limitation to the disclosure.

Here, the measurement space S may be divided into a plurality of measurement sub-spaces $S_0, S_1, \ldots,$ and $S_r$. The number of the measurement sub-spaces $S_0, S_1, \ldots,$ and $S_r$ may be $(G_H \cdot G_W)$. As shown in FIG. 5, in step S10, the first measurement sub-space is defined as $S_r$, and r=0. The alignment position of the pulsed electromagnetic wave beam $x_r$ is caused to rest at the first measurement sub-space ($S_r$, r=0), and the intensity of the pulsed electromagnetic wave beam $x_r$ are set to have a constant value greater than zero. Specifically, the system 100A of image reconstruction described herein includes an electromagnetic wave detector 120A having a sensing area H2. The hole H1 of the collimator 116, the sensing area H2 of the electromagnetic wave detector 120A, and the first measurement sub-space ($S_r$, r=0) may be substantially aligned to one another, and the intensity of the pulsed electromagnetic wave beam $x_r$ is set to have a constant value greater than zero (step S20).

The electromagnetic wave detector 120A then measures the first intensities $I_{01}(E_1), I_{01}(E_2)$ to $I_{0i}(E_M)$ of the electromagnetic wave beam $x_r$ passing through the first measurement sub-space ($S_r$, r=0) and corresponding to the photon energy levels $E_1, E_2, \ldots,$ and $E_M$ and records a first correspondence relation between the first intensities $I_{01}(E_1), I_{01}(E_2)$ to $I_{0i}(E_M)$ of the electromagnetic wave beam $x_r$ and the first measurement sub-space ($S_r$, r=0) in step S30. For instance, the first correspondence relation between the coordinate of the hole H1 (or the coordinate of the sensing area H2) and the first intensities is recorded. Particularly, the processing unit 140 described herein may be electrically connected to the electromagnetic wave detector 120A, so as to obtain the first intensities $I_{01}(E_1)$, $I_{01}(E_2)$ to $I_{01}(E_M)$ of the electromagnetic wave beam $x_r$ passing through the measurement sub-space $S_r$, and corresponding to the photon energy levels $E_1, E_2, \ldots$, and $E_M$ and record the first correspondence relation between the first intensities $I_{01}(E_1)$, $I_{01}(E_2)$ to $I_{01}(E_M)$ of the electromagnetic wave beam $x_r$ and the measurement sub-space $S_r$.

In step S40, the intensity of the pulsed electromagnetic wave beam $x_r$ is set to be zero. It is then determined whether the measurement space is the $(G_H \cdot G_W)^{th}$ measurement space, i.e., the last measurement space. That is, in step S50, whether r is equal to $(G_H \cdot G_W)$ is determined. If r is not equal to (GH·GW), 1 is added to the value of r (step S60), so as to cause the alignment position of the pulsed electromagnetic wave beam $x_r$ to rest at the next measurement sub-space ($S_r$, r=1), and the intensity of the pulsed electromagnetic wave beam $x_r$ is set to have a constant value greater than zero. That is, the hole H1 of the collimator 116 and the sensing area H2 of the electromagnetic wave detector 120A are substantially aligned to the next measurement sub-space ($S_r$, r=1), and the intensity of the pulsed electromagnetic wave beam $x_r$ is set to have the aforesaid constant value greater than zero (step S20).

In the period of setting the intensity of the pulsed electromagnetic wave beam $x_r$ to be zero (step S40), the control unit 130 may move the hole H1 of the collimator 116 and the sensing area H2 of the electromagnetic wave detector 120A to be aligned to the next measurement sub-space. In the present exemplary embodiment, the control unit 130 may together move the hole H1 of the collimator 116 and the sensing area of the electromagnetic wave detector 120A to be simultaneously aligned to the next measurement sub-space. When the electromagnetic wave detector 120A measures the first intensities corresponding to each measurement sub-space, the hole H1 of the collimator 116, each measurement sub-space, and the sensing area H2 of the electromagnetic wave detector 120 are substantially aligned to one another.

Specifically, the system 100A of image reconstruction described herein further includes a first mechanism 170 and a second mechanism 180. The collimator 116 is disposed on the first mechanism 170. The electromagnetic wave detector 120A is disposed on the second mechanism 180. Through the first mechanism 170 and the second mechanism 180, the control unit 130 causes the hole H1 of the collimator 116 and the sensing area H2 of the electromagnetic wave detector 120A to be moved simultaneously, such that the hole H1 of the collimator 116, the sensing area H2 of the electromagnetic wave detector 120A, and the to-be-measured measurement sub-space $S_r$ are simultaneously aligned to one another. However, in another exemplary embodiment of the disclosure, the hole H1 of the collimator 116 and the sensing area H2 of the electromagnetic wave detector 120A may be aligned to the to-be-measured measurement sub-space $S_r$ at different times, which should not be construed as a limitation to the disclosure.

To be specific, in the present exemplary embodiment, the first mechanism 160 includes two rails 172 having two different extension directions and a driver motor 174 connected to the rails 172. Similarly, the second mechanism 180 includes two rails 182 having two different extension directions and a motor 184 connected to the rails 182. The motors 174 and 184 are electrically connected to the control unit 130. The collimator 116 and the electromagnetic wave detector 120A are respectively disposed on the rails 172 and 182. Through the motors 174 and 184, the control unit 130 drives the collimator 116 and the electromagnetic wave detector 120A respectively disposed on the rails 172 and 182 to move, such that the hole H1 of the collimator 116 and the sensing area H2 of the electromagnetic wave detector 120A are aligned to the to-be-measured measurement sub-space $S_r$.

With reference to FIG. 5, the electromagnetic wave detector 120A measures the first intensities of the electromagnetic wave passing through the next measurement sub-space ($S_r$, r=1) and corresponding to the photon energy levels and records the first correspondence relation between the first intensities and the measurement sub-space ($S_r$, r=1) in step S30. The steps S40, S50, S60, S20, and S30 are cyclically performed until r is determined to be equal to ($G_H \cdot G_W$) in step S50, i.e., the first intensities of the electromagnetic wave passing through each measurement sub-space are all measured, and the first correspondence relations between the first intensities and the measurement sub-spaces are all recorded. After the first intensities of the electromagnetic wave passing through each measurement sub-space are all measured, and the first correspondence relations between the first intensities and the measurement sub-spaces are all recorded, the first intensity images may be obtained according to the first intensities of the electromagnetic wave beam passing through each of the measurement sub-spaces and the first correspondence relations between the first intensities and the measurement sub-spaces (step S70).

With reference to FIG. 6, particularly, the processing unit 140 may obtain the first intensity images according to the first intensities of the electromagnetic wave beam $x_r$ passing through each measurement sub-space $S_r$ and corresponding to the photon energy levels $E_1, E_2, \ldots$, and $E_M$ and the first correspondence relations between the first intensities and the measurement sub-spaces $S_r$.

As shown in FIG. 5 and FIG. 6, when the object O is placed in the measurement space S, the second intensity images of the electromagnetic wave passing through the object O and corresponding to the photon energy levels $E_1, E_2, \ldots$, and $E_M$ are measured (step S2). Namely, when the blocks $O_0$, $O_1, \ldots$, and $O_r$ are placed in the measurement sub-spaces $S_0$, $S_1, \ldots$, and $S_r$, the second intensities $I_{r2}(E_1)$, $I_{r2}(E_2)$ to $I_{r2}(E_M)$ of the electromagnetic wave beam $X_r$ passing through the block $O_r$ and corresponding to the photon energy levels $E_1, E_2, \ldots$, and $E_M$ are measured.

In the present embodiment, the step of measuring the second intensities $I_{r2}(E_1)$, $I_{r2}(E_2)$ to $I_{r2}(E_M)$ of the electromagnetic wave beam $X_r$ passing through the block $O_r$ and corresponding to the photon energy levels $E_1, E_2, \ldots$, and $E_M$ includes: causing the pulsed electromagnetic wave beam $x_r$ to scan the blocks $O_0, O_1, \ldots$, and $O_r$, wherein when the intensity of the pulsed electromagnetic wave beam $x_r$ is substantially zero, an alignment position of the pulsed electromagnetic wave beam $x_r$ is relatively moved from one of the blocks $O_0, O_1, \ldots$, and $O_r$ to another of the blocks $O_0$, $O_1, \ldots$, and $O_r$. When the intensity of the pulsed electromagnetic wave beam $x_r$ is substantially not zero, the alignment position of the pulsed electromagnetic wave beam $x_r$ is kept still with respect to the one of the blocks. When the alignment position of the pulsed electromagnetic wave beam $x_r$ respectively rests at the blocks $O_0, O_1, \ldots$, and $O_r$, the second intensities $I_{r2}(E_1)$, $I_{r2}(E_2)$ to $I_{r2}(E_M)$ of the pulsed electromagnetic wave beam $x_r$ passing through each of the blocks $O_0, O_1, \ldots$, and $O_r$ and corresponding to the photon energy levels $E_1, E_2, \ldots$, and $E_M$ are respectively measured.

As shown in FIG. 6, the control unit 130 causes the pulsed electromagnetic wave beam $x_r$ to scan the blocks $O_r$ of the object O by moving the collimator 116. When the intensity of the pulsed electromagnetic wave beam $x_r$ is substantially zero, the control unit 130 moves the pulsed electromagnetic wave beam $x_r$ from one of the blocks $O_0, O_1, \ldots,$ and $O_r$ to another of the blocks $O_0, O_1, \ldots,$ and $O_r$. When the intensity of the pulsed electromagnetic wave beam $x_r$ is substantially not zero (e.g., when the intensity respectively has a constant value), the control unit 130 controls the pulsed electromagnetic wave beam $x_r$ to be kept still with respect to the object O, and the electromagnetic detector 120A of the system 100A of image reconstruction respectively measures the second intensities $I_{r2}(E_1), I_{r2}(E_2)$ to $I_{r2}(E_M)$ of the pulsed electromagnetic wave beam $x_r$ passing through each of the blocks $O_0, O_1, \ldots,$ and $O_r$ when the alignment position of the pulsed electromagnetic wave beam $x_r$ respectively rests at the blocks $O_0, O_1, \ldots,$ and $O_r$.

As shown in FIG. 5 and FIG. 6, the method of measuring the second intensity images of the electromagnetic wave beam passing through the object O and corresponding to the photon energy levels $E_1, E_2, \ldots,$ and $E_M$ includes steps S11, S12, S13, S14, S15, and S16, which will be elaborated hereinafter.

In the present exemplary embodiment, the object O may be divided into a plurality of blocks $O_0, O_1, \ldots,$ and $O_r$, and the number of the blocks $O_0, O_1, \ldots,$ and $O_r$ may be $(G_H \cdot G_W)$. As shown in FIG. 5, in step S11, the first object is defined as $O_r$, and r=0. The pulsed electromagnetic wave beam $x_r$ is constantly aligned to the first block ($O_r$, r=0), and the intensity of the pulsed electromagnetic wave beam $x_r$ is set to have a constant value greater than zero. Specifically, the hole H1 of the collimator 116, the sensing area H2 of the electromagnetic wave detector 120A, and the first block ($O_r$, r=0) may be substantially aligned to one another, and the intensity of the pulsed electromagnetic wave beam $x_r$ is set to have a constant value greater than zero (step S12).

The electromagnetic wave detector 120A then measures the second intensities $I_{02}(E_1), I_{02}(E_2)$ to $I_{02}(E_M)$ of the electromagnetic wave beam $x_r$ passing through the first block ($O_r$, r=0) and corresponding to the photon energy levels $E_1, E_2, \ldots,$ and $E_M$ and records a second correspondence relation between the second intensities $I_{02}(E_1), I_{02}(E_2)$ to $I_{02}(E_M)$ and the block ($O_r$, r=0) in step S13. For instance, the second correspondence relation between the coordinate of the hole H1 (or the coordinate of the sensing area H2) and the second intensities $I_{02}(E_1), I_{02}(E_2)$ to $I_{02}(E_M)$ is recorded. Particularly, the processing unit 140 described herein may be electrically connected to the electromagnetic wave detector 120A, so as to obtain the second intensities $I_{02}(E_1), I_{02}(E_2)$ to $I_{02}(E_M)$ of the electromagnetic wave beam $x_r$ passing through the block $O_r$ and corresponding to the photon energy levels $E_1, E_2, \ldots,$ and $E_M$ and record the second correspondence relation between the second intensities $I_{02}(E_1), I_{02}(E_2)$ to $I_{02}(E_M)$ of the electromagnetic wave beam $x_r$ and the block $O_r$.

In step S14, the intensity of the pulsed electromagnetic wave beam $x_r$ is set to be zero. According to the first intensities $I_{01}(E_1), I_{01}(E_2)$ to $I_{01}(E_M)$ of the electromagnetic wave beam $x_r$ passing through the first measurement sub-space ($S_r$, r=0) and corresponding to the photon energy levels $E_1, E_2, \ldots,$ and $E_M$, the second intensities $I_{02}(E_1), I_{02}(E_2)$ to $I_{02}(E_M)$ of the electromagnetic wave beam $x_r$ passing through the first block ($O_r$, r=0) and corresponding to the photon energy levels $E_1, E_2, \ldots,$ and $E_M$, the inverse matrix $W^{-1}$, and the aforesaid equation (3), the first attenuation coefficients $\mu_{r1}(E_1), \mu_{r2}(E_1)$ to $\mu_{rN}(E_1)$ of the first block ($O_r$, r=0) respectively corresponding to the first, second to $N^{th}$ components irradiated by the electromagnetic wave beam $x_r$ corresponding to the first photon energy level $E_1$ are calculated (step S323). The detailed method of calculating the first attenuation coefficients may be referred to as the description provided in the first exemplary embodiment. In particular, the processing unit 140 described in the present exemplary embodiment and shown in FIG. 6 may perform the above-mentioned step of calculating the first attenuation images.

It is then determined whether the measured block is the $(G_H \cdot G_W)^{th}$ block, i.e., the last block. That is, in step S15, whether r is equal to $(G_H \cdot G_W)$ is determined. If r is not equal to (GH·GW), 1 is added to the value of r (step S16), so as to cause the alignment position of the pulsed electromagnetic wave beam $x_r$ to rest at the next block ($O_r$, r=1), and the intensity of the pulsed electromagnetic wave beam $x_r$ is set to have a constant value greater than zero. That is, the hole H1 of the collimator 116 and the sensing area H2 of the electromagnetic wave detector 120A are substantially aligned to the next block ($O_r$, =1), and the intensity of the pulsed electromagnetic wave beam $x_r$ is set to have the aforesaid constant value greater than zero (step S12).

In the period of setting the intensity of the pulsed electromagnetic wave beam $x_r$ to be zero (step S14), the control unit 130 may move the hole H1 of the collimator 116 and the sensing area H2 of the electromagnetic wave detector 120A to be aligned to the next block. In the present exemplary embodiment, the control unit 130 may together move the hole H1 of the collimator 116 and the sensing area of the electromagnetic wave detector 120A to be simultaneously aligned to the next block. When the electromagnetic wave detector 120A measures the second intensities corresponding to each block, the hole H1 of the collimator 116, each block, and the sensing area H2 of the electromagnetic wave detector 120 are substantially aligned to one another.

Through the first mechanism 170 and the second mechanism 180, the control unit 130 causes the hole H1 of the collimator 116 and the sensing area H2 of the electromagnetic wave detector 120A to be moved simultaneously, such that the hole H1 of the collimator 116, the sensing area H2 of the electromagnetic wave detector 120A, and the to-be-measured block $O_r$ are simultaneously aligned to one another. However, in another exemplary embodiment of the disclosure, the hole H1 of the collimator 116 and the sensing area H2 of the electromagnetic wave detector 120A may be aligned to the to-be-measured block $O_r$ at different times, which should not be construed as a limitation to the disclosure.

With reference to FIG. 5, the electromagnetic wave detector 120A measures the second intensities of the electromagnetic wave beam $x_r$ passing through the next block ($O_r$, r=1) and corresponding to the photon energy levels $E_1, E_2$ to $E_M$ and records the second correspondence relation between the second intensities and the block ($O_r$, r=1) in step S13. The steps S14, S323, S15, S16, and S12 are cyclically performed until r is determined to be equal to $(G_H \cdot G_W)$ in step S15, i.e., the second intensities of the electromagnetic wave passing through each block are all measured, the second correspondence relations between the second intensities and the blocks are all recorded, and the first attenuation coefficients corresponding to the blocks are all calculated. Thereby, the attenuation images of the object respectively corresponding to the components may be obtained. The method of obtaining the attenuation images of all blocks of the object respectively corresponding to the components may be referred to as the description in the first exemplary embodiment.

In the present exemplary embodiment, after the second intensities $I_{r2}(E_1), I_{r2}(E_2)$ to $I_{r2}(E_M)$ of the electromagnetic wave beam $X_r$ passing through a certain block $O_r$ and corresponding to the photon energy levels $E_1, E_2, \ldots,$ and $E_M$ are all measured, and after the second correspondence relations between the second intensities $I_{r2}(E_1), I_{r2}(E_2)$ to $I_{r2}(E_M)$ and the block $O_r$ are all recorded, and the first attenuation coefficients corresponding to the blocks are all calculated, the first attenuation coefficients of the block $O_r$ respectively corresponding to the components irradiated by the electromagnetic wave beam $x_r$ corresponding to a certain photon energy level are calculated according to the first intensities $I_{r1}(E_1)$, $I_{r1}(E_2)$ to $I_{r1}(E_M)$ of the electromagnetic wave beam $x_r$ passing through the measurement sub-space $S_r$ and corresponding to the photon energy levels $E_1, E_2, \ldots$, and $E_M$, the second intensities $I_{r2}(E_1)$, $I_{r2}(E_2)$ to $I_{r2}(E_M)$ of the electromagnetic wave beam $x_r$ passing through the block $O_r$, and corresponding to the photon energy levels $E_1, E_2, \ldots$, and $E_M$, the inverse matrix $W^{-1}$, and the aforesaid equation (3). Further, the attenuation images of the object O respectively corresponding to the components are obtained.

However, the disclosure is not limited thereto; in another exemplary embodiment, the second intensity images may be obtained according to the second intensities of the electromagnetic wave beam passing through each of the blocks and the second correspondence relations between the second intensities and the blocks after the second intensities of the electromagnetic wave passing through the blocks are all measured and after the second correspondence relations between the second intensities and the blocks are all recorded. The attenuation images of the object respectively corresponding to the components are then calculated according to the attenuation coefficient of each substance respectively having a plurality of components irradiated by the electromagnetic wave corresponding to each of the photon energy levels, the thickness of each substance in the transmission direction of the electromagnetic wave corresponding to each of the photon energy levels, the first intensity images, and the second intensity images.

In the method and the system of image reconstruction described herein, the pulsed electromagnetic wave beam passes through each measurement sub-space (and each block) one by one, and when the pulsed electromagnetic wave beam moves from one measurement sub-space (and one block) to the next measurement sub-space (and the next block), the intensity of the pulsed electromagnetic wave beam is substantially zero. Therefore, the measured first intensities corresponding to each measurement sub-space (and the measured second intensities corresponding to each block) are not apt to be affected by other factors, such that the attenuation images reconstructed by applying the method and the system of image reconstruction described herein may precisely exhibit the actual condition and components within the object.

Third Exemplary Embodiment

The method and the system of image construction described herein are similar to those provided in the second exemplary embodiment, and thus the same steps and the same components are represented by the same reference numbers.

Figure 7:
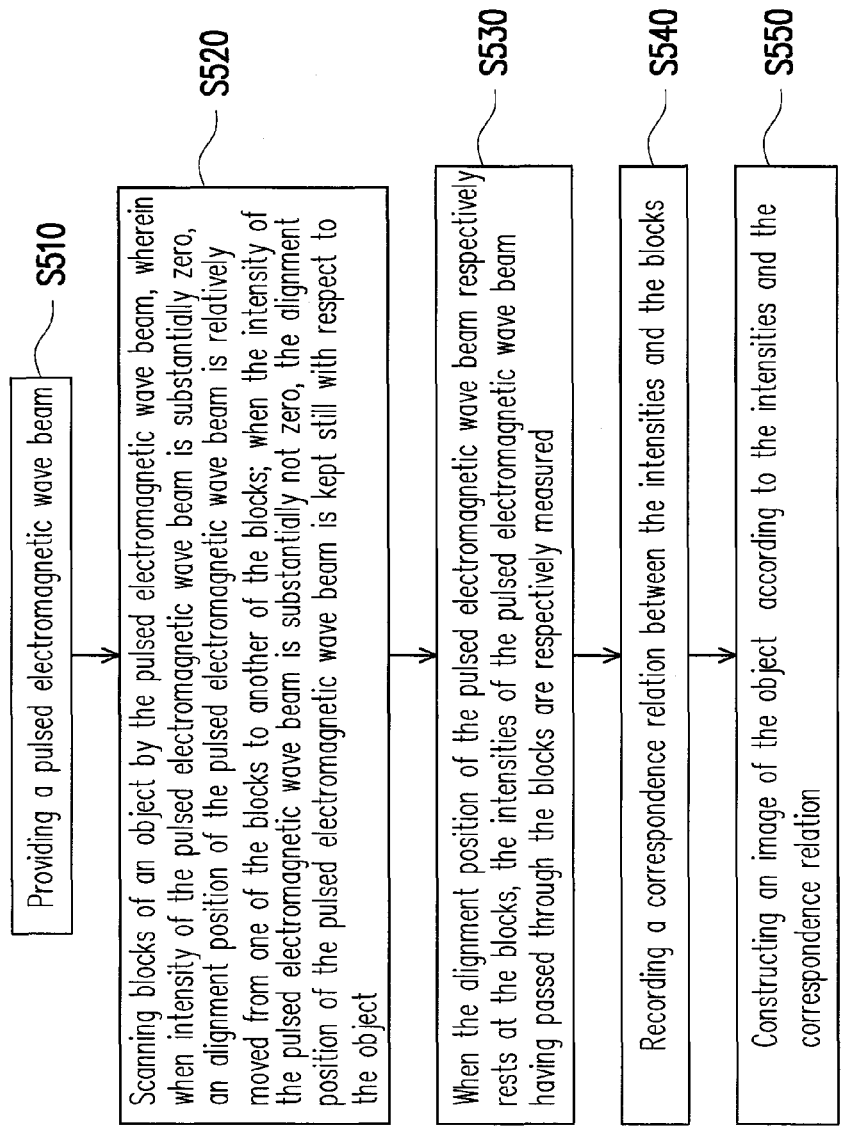
FIG. 7 is a flow chart illustrating a method of image construction according to an exemplary embodiment of the disclosure.
Figure 8:
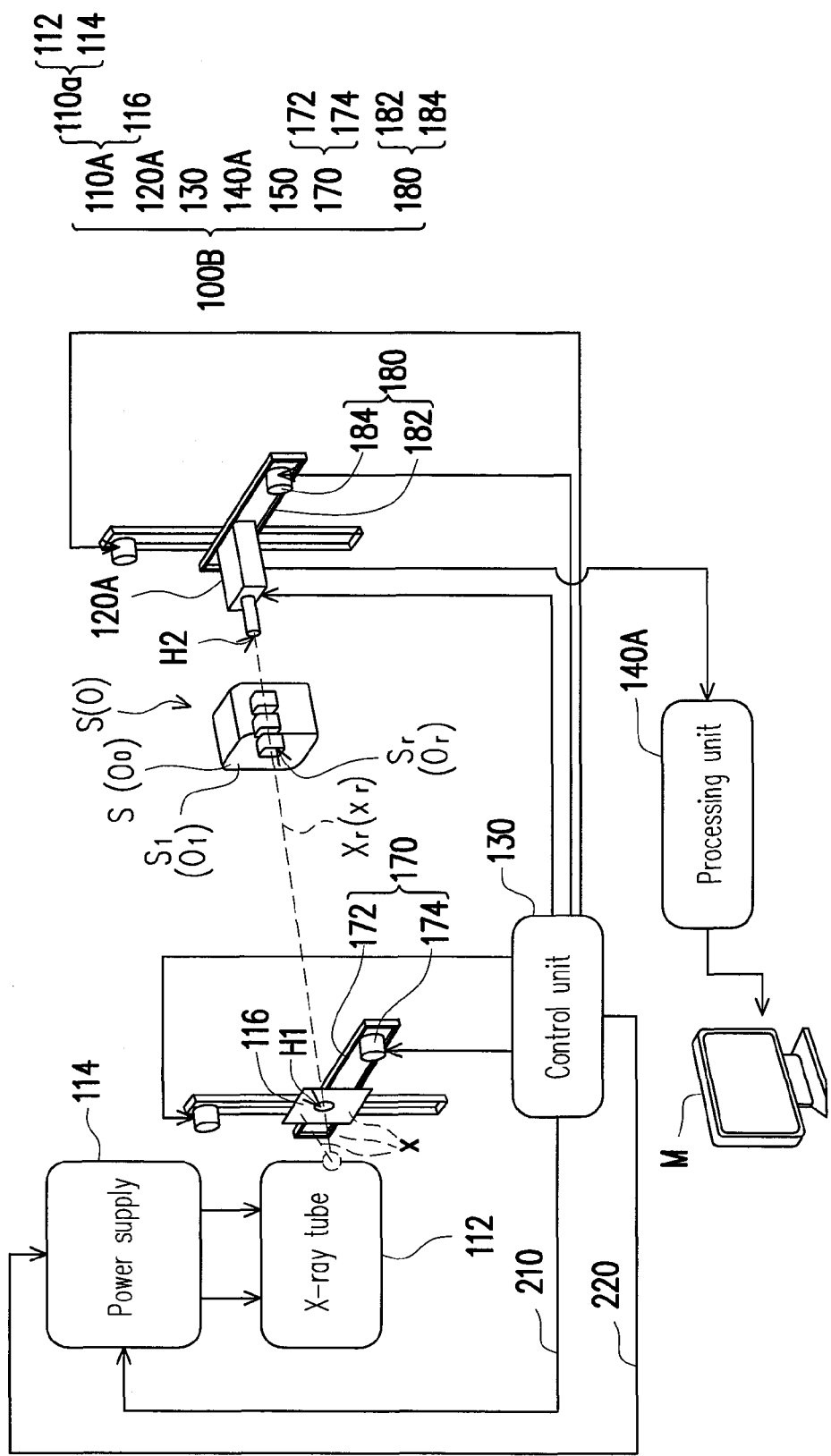
FIG. 8 illustrates a system of image construction according to an exemplary embodiment of the disclosure.

FIG. 7 is a flow chart illustrating a method of image construction according to an exemplary embodiment of the disclosure. FIG. 8 illustrates a system of image construction according to an exemplary embodiment of the disclosure. Note that the method of image construction shown in FIG. 7 is applicable to the system of image construction depicted in FIG. 8. With reference to FIG. 7 and FIG. 8, in the present exemplary embodiment, the method and the system 100B of image construction are provided for constructing an image of an object S. In step S510, a pulsed electromagnetic wave beam $x_r$ is provided. Specifically, a pulsed electromagnetic wave x is provided and then transmitted to a collimator 116 having a hole H1. Here, a portion of the pulsed electromagnetic wave x passes through the hole H1 of the collimator 116 to form the pulsed electromagnetic wave beam $x_r$.

In the present exemplary embodiment, the system 100B of image construction includes a pulsed electromagnetic wave beam providing unit 110A. The pulsed electromagnetic wave providing unit 110A includes a pulsed electromagnetic wave source 110a and a collimator 116, and the pulsed electromagnetic wave source 110a provides the pulsed electromagnetic wave x. The pulsed electromagnetic wave source 110a includes an X-ray tube 112 and a power supply 114. In the present exemplary embodiment, the system 100B of image construction may further include a control unit 130 that is electrically connected to the pulsed electromagnetic wave providing unit 110A. The control unit 130 may respectively control the voltage and the current input from the power supply 114 to the X-ray tube 112 through transmission channels 210 and 220 and thereby control the X-ray tube 112 to emit the pulsed electromagnetic wave x. The collimator 116 described herein is disposed on a transmission path of the pulsed electromagnetic wave x. Besides, the collimator 116 has a hole H1. A portion of the pulsed electromagnetic wave x passes through the hole H1 of the collimator 116 to form the pulsed electromagnetic wave beam $x_r$.

A plurality of blocks $O_0, O_1, \ldots$, and $O_r$ of the object O are scanned by the pulsed electromagnetic wave beam $x_r$. When intensity of the pulsed electromagnetic wave beam $x_r$ is substantially zero, the pulsed electromagnetic wave beam $x_r$ is moved from one of the blocks $O_0, O_1, \ldots$, and $O_r$ and aligned to another of the blocks $O_0, O_1, \ldots$, and $O_r$; when the intensity of the pulsed electromagnetic wave beam $x_r$ is substantially not zero, the alignment position of the pulsed electromagnetic wave beam $x_r$ is kept still with respect to the object O (step S520). As shown in FIG. 8, the control unit 130 described herein causes the pulsed electromagnetic wave beam $x_r$ to scan the blocks $O_0, O_1, \ldots$, and $O_r$ of the object O by moving the collimator 116. When the intensity of the pulsed electromagnetic wave beam $x_r$ is substantially zero, the control unit 130 moves the pulsed electromagnetic wave beam $x_r$ from one of the blocks $O_0, O_1, \ldots$, and $O_r$ to another of the blocks $O_0, O_1, \ldots$, and $O_r$. Besides, when the intensity of the pulsed electromagnetic wave beam $x_r$ is substantially not zero (e.g., when the intensity of the pulsed electromagnetic wave beam $x_r$ has a constant value), the control unit 130 causes the alignment position of the pulsed electromagnetic wave beam $x_r$ to be kept still with respect to one block $O_r$.

When the alignment position of the pulsed electromagnetic wave beam $x_r$ respectively rests at the blocks $O_0, O_1, \ldots$, and $O_r$, the intensities of the pulsed electromagnetic wave beam $x_r$ passing through the blocks $O_0, O_1, \ldots$, and $O_r$ are respectively measured (step S530). Specifically, the system 100B of image construction includes an electromagnetic wave detector 120A. When the pulsed electromagnetic wave beam $x_r$ respectively rests at the blocks $O_0, O_1, \ldots$, and $O_r$, the electromagnetic wave detector 120A respectively measures the intensities of the pulsed electromagnetic wave beam $x_r$ passing through the blocks $O_0, O_1, \ldots$, and $O_r$. In the present exemplary embodiment, the control unit 130 may together move the hole H1 of the collimator 116 and the electromagnetic wave detector 120A, and the electromagnetic wave detector 120A is configured to measure the intensities of the pulsed electromagnetic wave beam $x_r$. Besides, when the electromagnetic wave detector 120A measures the intensities of the pulsed electromagnetic wave beam $x_r$, the control unit 130 causes the hole H1 of the collimator 116, a sensing area H2 of the electromagnetic wave detector 120A, and each of the blocks $O_0, O_1, \ldots$, and $O_r$ to be substantially aligned to one another.

Specifically, the system 100B of image construction described herein further includes a first mechanism 170 and a second mechanism 180. The collimator 116 is disposed on the first mechanism 170. The electromagnetic wave detector 120A is disposed on the second mechanism 180. Through the first mechanism 170 and the second mechanism 180, the control unit 130 allows the hole H1 of the collimator 116 and the sensing area H2 of the electromagnetic wave detector 120A to be moved simultaneously, such that the hole H1 of the collimator 116, the sensing area H2 of the electromagnetic wave detector 120A, and the to-be-measured block $O_r$ are simultaneously aligned to one another. However, in another exemplary embodiment of the disclosure, the hole H1 of the collimator 116 and the sensing area H2 of the electromagnetic wave detector 120A may be aligned to the to-be-measured block $O_r$ at different times, which should not be construed as a limitation to the disclosure.

A correspondence relation between the intensities of the pulsed electromagnetic wave beam and the blocks is recorded (step S540). The image of the object O is constructed according to the intensities of the pulsed electromagnetic wave beam and the correspondence relation (step S550). Specifically, the system 100B of image construction includes the processing unit 140A. The processing unit 140A records a correspondence relation between the intensities of the pulsed electromagnetic wave beam and the blocks $O_0, O_1, \ldots,$ and $O_r$. For instance, when the electromagnetic wave detector 120A measures the intensities of the pulsed electromagnetic wave beam, the processing unit 140A records the relation between the intensities and the coordinate of the sensing area H2 of the electromagnetic wave detector 120A or the relation between the intensities and the coordinate of the hole H1 of the collimator 116. According to the intensities of the pulsed electromagnetic wave beam and the correspondence relation, the processing unit 140A constructs the image of the object O.

In the method and the system of image construction described herein, the pulsed electromagnetic wave beam scans each block one by one, and when the pulsed electromagnetic wave beam moves from one block to the next block, the intensity of the pulsed electromagnetic wave beam is substantially zero. Therefore, the measured intensities corresponding to each block are not apt to be affected by other factors, such that the image of the object may be precisely constructed by applying the method and the system of image construction described herein.

To sum up, according to the method and the system of image reconstruction described herein, the attenuation images of the object having the components may be calculated by applying the aforesaid data processing method, and each component of the object may respectively constitute an attenuation image.

Besides, in the method and the system of image reconstruction described in another exemplary embodiment, the attenuation images of the object having the components may be obtained by performing a one-time scanning process (or a one-time image obtaining process) on the object, such that the object does not absorb excessive amount of radiation, and that the resultant damages to the object during the radiographic examination may be mitigated.

Moreover, in the method and system of image reconstruction described in another exemplary embodiment, the pulsed electromagnetic wave beam passes through each measurement sub-space (and each block) one by one, and when the pulsed electromagnetic wave beam moves from one measurement sub-space (and one block) to the next measurement sub-space (and the next block), the intensity of the pulsed electromagnetic wave beam is substantially zero. Accordingly, the measured first intensities corresponding to each measurement sub-space (and the measured second intensities corresponding to each block) are not apt to be affected by other factors, such that the attenuation images reconstructed by applying the method and the system of image reconstruction described in another exemplary embodiment may precisely exhibit the actual condition and components within the object.

In another aspect, according to the method and the system of image construction described in an exemplary embodiment, the pulsed electromagnetic wave beam scans each block one by one, and when the pulsed electromagnetic wave beam moves from one block to the next block, the intensity of the pulsed electromagnetic wave beam is substantially zero. Hence, the measured intensities corresponding to each block are not apt to be affected by other factors, such that the image of the object may be precisely constructed by applying the method and the system of image construction described herein.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A method of image reconstruction for reconstructing an image of an object, the method comprising:
   when the object is not placed in a measurement space, measuring a plurality of first intensity images of an electromagnetic wave passing through the measurement space and respectively corresponding to a plurality of photon energy levels;
   when the object is placed in the measurement space, measuring a plurality of second intensity images of the electromagnetic wave passing through the object and respectively corresponding to the photon energy levels;
   providing data in a database, the data comprising an attenuation coefficient of each of a plurality of substances respectively having a plurality of components irradiated by the electromagnetic wave corresponding to each of the photon energy levels and a thickness of each of the substances in a transmission direction of the electromagnetic wave corresponding to the photon energy level; and
   calculating a plurality of attenuation images of the object respectively corresponding to the components according to the data in the database, the first intensity images, and the second intensity images.

2. The method as recited in claim 1, wherein the object is divided into a plurality of blocks, the measurement space is divided into a plurality of measurement sub-spaces, the blocks are predetermined to be placed in the measurement sub-spaces, each of the measurement sub-spaces is passed through by one electromagnetic wave beam, and the electromagnetic wave beam is a portion of the electromagnetic wave; when the object is not placed in the measurement space, the step of measuring the first intensity images of the electromagnetic wave passing through the measurement space and corresponding to the photon energy levels comprising: when the blocks are not placed in the measurement sub-spaces, measuring a plurality of first intensities of the electromagnetic wave beam passing through each of the measurement sub-spaces and corresponding to the photon energy levels, wherein the first intensities of the electromagnetic wave beam passing through the measurement sub-spaces and corresponding to the photon energy levels respectively constitute the first intensity images; when the object is placed in the measurement space, the step of measuring the second intensity images of the electromagnetic wave passing through the object and corresponding to the photon energy levels comprising: when the blocks are respectively placed in the measurement sub-spaces, measuring a plurality of second intensities of the electromagnetic wave beam passing through each of the blocks and corresponding to the photon energy levels, wherein the second intensities of the electromagnetic wave beam passing through the blocks and corresponding to the photon energy levels respectively constitute the second intensity images; and the step of calculating the attenuation images of the object respectively corresponding to the components according to the data in the database, the first intensity images, and the second intensity images comprising: calculating a plurality of first attenuation coefficients of each of the blocks respectively corresponding to each of the components irradiated by the electromagnetic wave beam corresponding to the photon energy levels according to the first intensities of the electromagnetic wave beam passing through each of the measurement sub-spaces and corresponding to the photon energy levels, the second intensities of the electromagnetic wave beam passing through each of the blocks and corresponding to the photon energy levels, the attenuation coefficients of the substances, and the thicknesses of the substances, wherein the first attenuation coefficients constitute the attenuation images.

3. The method as recited in claim 2, wherein the components comprise a first component, a second component to an $N^{th}$ component, N is a positive integer greater than or equal to 2, the photon energy levels comprise a first photon energy level, a second photon energy level to an $M^{th}$ photon energy level, M is a positive integer greater than or equal to N, and the step of calculating the first attenuation coefficients of each of the blocks respectively corresponding to the first, second to $N^{th}$ components irradiated by the electromagnetic wave beam corresponding to the first photon energy level according to the first intensities of the electromagnetic wave beam passing through each of the measurement sub-spaces and corresponding to the photon energy levels, the second intensities of the electromagnetic wave beam passing through each of the blocks and corresponding to the photon energy levels, the attenuation coefficients of the substances, and the thicknesses of the substances comprises:

according to the attenuation coefficients of the substances, calculating conversion relations between the attenuation coefficient of the first component irradiated by the corresponding electromagnetic wave beam corresponding to the first photon energy level and the attenuation coefficients of the first component irradiated by the electromagnetic wave corresponding to the second to the $M^{th}$ photon energy levels, conversion relations between the attenuation coefficient of the second component irradiated by the corresponding electromagnetic wave beam corresponding to the first photon energy level and the attenuation coefficients of the second component irradiated by the electromagnetic wave corresponding to the second to the $M^{th}$ photon energy levels, to conversion relations between the attenuation coefficient of the $N^{th}$ component irradiated by the corresponding electromagnetic wave beam corresponding to the first photon energy level and the attenuation coefficients of the $N^{th}$ component irradiated by the electromagnetic wave corresponding to the second to the $M^{th}$ photon energy levels;

establishing a conversion matrix according to the conversion relations;

establishing a proportion matrix according to the first intensities of the electromagnetic wave beam passing through each of the measurement sub-spaces and corresponding to the photon energy levels and the second intensities of the electromagnetic wave beam passing through each of the blocks and corresponding to the photon energy levels; and calculating the first attenuation coefficients of each of the blocks respectively corresponding to the first, second to $N^{th}$ components irradiated by the electromagnetic wave beam corresponding to the first photon energy level according to the proportion matrix, the conversion matrix, and the thicknesses of the substances.

4. The method as recited in claim 3, wherein the first photon energy level, the second photon energy level to the $M^{th}$ photon energy level are respectively represented as $E_1$, $E_2$ to $E_M$, the conversion relations between the attenuation coefficient of the first component irradiated by the electromagnetic wave corresponding to the first photon energy level and the attenuation coefficients of the first component irradiated by the electromagnetic wave corresponding to the second to the $M^{th}$ photon energy levels are respectively represented as $w(\mu_{r1},E_2)$ to $w(\mu_{r1},E_M)$, the conversion relations between the attenuation coefficient of the second component irradiated by the electromagnetic wave corresponding to the first photon energy level and the attenuation coefficients of the second component irradiated by the electromagnetic wave corresponding to the second to the $M^{th}$ photon energy levels are respectively represented as $w(\mu_{r2},E_2)$ to $w(\mu_{r2},E_M)$, the conversion relations between the attenuation coefficient of the $N^{th}$ component irradiated by the electromagnetic wave corresponding to the first photon energy level and the attenuation coefficients of the $N^{th}$ component irradiated by the electromagnetic wave corresponding to the second to the $M^{th}$ photon energy levels are respectively represented as $w(\mu_{rN},E_2)$ to $w(\mu_{rN},E_M)$, the conversion matrix is represented as W, and $$W = \begin{bmatrix} 1 & 1 & \cdots & 1 \\ w(\mu_{r1},E_2) & w(\mu_{r2},E_2) & \cdots & w(\mu_{rN},E_2) \\ \vdots & \vdots & \ddots & \vdots \\ w(\mu_{r1},E_M) & w(\mu_{r2},E_M) & \cdots & w(\mu_{rN},E_M) \end{bmatrix}$$

wherein the first intensities of the electromagnetic wave beam passing through each of the measurement sub-spaces and corresponding to the first, second to $M^{th}$ photon energy levels are respectively represented as $I_{r1}(E_1)$, $I_{r1}(E_2)$ to $I_{r1}(E_M)$, the second intensities of the electromagnetic wave beam passing through each of the blocks and corresponding to the first, second to the $M^{th}$ photon energy levels are respectively represented as $I_{r2}(E_1)$, $I_{r2}(E_2)$, to $I_{r2}(E_M)$, the proportion matrix is represented as $T_r$, and $$T_r = \begin{bmatrix} -\ln\left(\frac{I_{r2}(E_1)}{I_{r1}(E_1)}\right) \\ -\ln\left(\frac{I_{r2}(E_2)}{I_{r1}(E_2)}\right) \\ \vdots \\ -\ln\left(\frac{I_{r2}(E_M)}{I_{r1}(E_M)}\right) \end{bmatrix}$$

wherein the thickness of the substance having the first component, the thickness of the substance having the second component to the thickness of the substance having the $N^{th}$ component are respectively represented as $t_1$, $t_2$ to $t_N$, the first attenuation coefficients of each of the blocks respectively corresponding to the first, second to $N^{th}$ components irradiated by the electromagnetic wave beam corresponding to the first photon energy level are respectively represented as $\mu_{r1}(E_1)$, $\mu_{r1}(E_i)$ to $\mu_{rN}(E_1)$, and the step of calculating the first attenuation coefficients of each of the blocks respectively corresponding to the first, second to $N^{th}$ components irradiated by the electromagnetic wave beam corresponding to the first photon energy level according to the proportion matrix, the conversion matrix, and the thicknesses of the substances comprises: calculating the first attenuation coefficients of each of the blocks respectively corresponding to the first, second to $N^{th}$ components irradiated by the electromagnetic wave beam corresponding to the first photon energy level by an equation (1):

$$\begin{bmatrix} \mu_{r1}(E_1) \cdot t_1 \\ \mu_{r2}(E_1) \cdot t_2 \\ \vdots \\ \mu_{rN}(E_1) \cdot t_N \end{bmatrix} = W^{-1} \cdot T_r. \quad (1)$$

5. The method as recited in claim 2, wherein the step of measuring the first intensities of the electromagnetic wave beam passing through each of the measurement sub-spaces and corresponding to the photon energy levels comprises: causing the electromagnetic wave beams to simultaneously and respectively pass through the measurement sub-spaces and simultaneously measuring the first intensities of the electromagnetic wave beams passing through the measurement sub-spaces and corresponding to the photon energy levels, and the step of measuring the second intensities of the electromagnetic wave beam passing through each of the blocks and corresponding to the photon energy levels comprises: causing the electromagnetic wave beams to simultaneously and respectively pass through the blocks and simultaneously measuring the second intensities of the electromagnetic wave beams passing through the blocks and corresponding to the photon energy levels.

6. The method as recited in claim 5, wherein the first and second intensities of the electromagnetic wave beams have constant values during a period of measuring the first intensity images and the second intensity images.

7. The method as recited in claim 5, further comprising:
before causing the electromagnetic wave beams to simultaneously and respectively pass through the measurement sub-spaces and the blocks, filtering out part of the electromagnetic wave beams having photon energy less than a minimum of the photon energy levels.

8. A system of image reconstruction for reconstructing an image of an object, the system comprising:
an electromagnetic wave providing unit providing an electromagnetic wave;
an electromagnetic wave detector measuring a plurality of first intensity images of the electromagnetic wave passing through a measurement space and corresponding to a plurality of photon energy levels when the object is not placed in the measurement space and measuring a plurality of second intensity images of the electromagnetic wave passing through the object and corresponding to the photon energy levels when the object is placed in the measurement space; and
a processing unit, data in a database comprising an attenuation coefficient of each of a plurality of substances respectively having a plurality of components irradiated by the electromagnetic wave corresponding to each of the photon energy levels and a thickness of each of the substances in a transmission direction of the electromagnetic wave corresponding to the photon energy level, the processing unit calculating a plurality of attenuation images of the object respectively corresponding to the components according to the data in the database, the first intensity images, and the second intensity images.

9. The system as recited in claim 8, wherein the object is divided into a plurality of blocks, the measurement space is divided into a plurality of measurement sub-spaces, the blocks are predetermined to be placed in the measurement sub-spaces, each of the measurement sub-spaces is passed through by one electromagnetic wave beam, and the electromagnetic wave beam is a portion of the electromagnetic wave, when the blocks are not placed in the measurement sub-spaces, the electromagnetic wave detector measures a plurality of first intensities of the electromagnetic wave beam passing through each of the measurement sub-spaces and corresponding to the photon energy levels, when the blocks are respectively placed in the measurement sub-spaces, the electromagnetic wave detector measures a plurality of second intensities of the electromagnetic wave beam passing through each of the blocks and corresponding to the photon energy levels, the first intensities of the electromagnetic wave beam passing through the measurement sub-spaces and corresponding to the photon energy levels respectively constitute the first intensity images, the second intensities of the electromagnetic wave beam passing through the blocks and corresponding to the photon energy levels respectively constitute the second intensity images, the processing unit calculates a plurality of first attenuation coefficients of each of the blocks respectively corresponding to each of the components irradiated by the electromagnetic wave beam corresponding to the photon energy levels according to the first intensities of the electromagnetic wave beam passing through each of the measurement sub-spaces and corresponding to the photon energy levels, the second intensities of the electromagnetic wave beam passing through each of the blocks and corresponding to the photon energy levels, the attenuation coefficients of the substances, and the thicknesses of the substances, and the first attenuation coefficients constitute the attenuation images.

10. The system as recited in claim 9, wherein the components comprise a first component, a second component to an $N^{th}$ component, N is a positive integer greater than or equal to 2, the photon energy levels comprise a first photon energy level, a second photon energy level to an $M^{th}$ photon energy level, M is a positive integer greater than or equal to N, the processing unit calculates conversion relations between the attenuation coefficient of the first component irradiated by the electromagnetic wave corresponding to the first photon energy level and the attenuation coefficients of the first component irradiated by the electromagnetic wave corresponding to the second to the $M^{th}$ photon energy levels, conversion relations between the attenuation coefficient of the second component irradiated by the electromagnetic wave corresponding to the first photon energy level and the attenuation coefficients of the second component irradiated by the electromagnetic wave corresponding to the second to the $M^{th}$ photon energy levels, to conversion relations between the attenuation coefficient of the $N^{th}$ component irradiated by the electromagnetic wave corresponding to the first photon energy level and the attenuation coefficients of the $N^{th}$ component irradiated by the electromagnetic wave corresponding to the second to the $M^{th}$ photon energy levels according to the attenuation coefficients of the substances, the processing unit establishes a conversion matrix according to the conversion relations and establishes a proportion matrix according to the first intensities of the electromagnetic wave beam passing through each of the measurement sub-spaces and corresponding to the photon energy levels and the second intensities of the electromagnetic wave beam passing through each of the blocks and corresponding to the photon energy levels, and the processing unit calculates the first attenuation coefficients of each of the blocks respectively corresponding to the first, second to $N^{th}$ components irradiated by the electromagnetic wave beam corresponding to the first photon energy level according to the proportion matrix, the conversion matrix, and the thicknesses of the substances.

11. The system as recited in claim 10, wherein the first photon energy level, the second photon energy level to the $M^{th}$ photon energy level are respectively represented as $E_1$, $E_2$ to $E_M$, the conversion relations between the attenuation coefficient of the first component irradiated by the electromagnetic wave corresponding to the first photon energy level and the attenuation coefficients of the first component irradiated by the electromagnetic wave corresponding to the second to the $M^{th}$ photon energy levels are respectively represented as $w(\mu_{r1}, E_2)$ to $w(\mu_{r1}, E_M)$, the conversion relations between the attenuation coefficient of the second component irradiated by the electromagnetic wave corresponding to the first photon energy level and the attenuation coefficients of the second component irradiated by the electromagnetic wave corresponding to the second to the $M^{th}$ photon energy levels are respectively represented as $w(\mu_{r2}, E_2)$ to $w(\mu_{r2}, E_M)$, the conversion relations between the attenuation coefficient of the $N^{th}$ component irradiated by the electromagnetic wave corresponding to the first photon energy level and the attenuation coefficients of the $N^{th}$ component irradiated by the electromagnetic wave corresponding to the second to the $M^{th}$ photon energy levels are respectively represented as $w(\mu_{rN}, E_2)$ to $w(\mu_{rN}, E_M)$, the conversion matrix is represented as W, and:

$$W = \begin{bmatrix} 1 & 1 & \cdots & 1 \\ w(\mu_{r1}, E_2) & w(\mu_{r2}, E_2) & \cdots & w(\mu_{rN}, E_2) \\ \vdots & \vdots & \ddots & \vdots \\ w(\mu_{r1}, E_M) & w(\mu_{r2}, E_M) & \cdots & w(\mu_{rN}, E_M) \end{bmatrix}$$

wherein the first intensities of the electromagnetic wave beam passing through each of the measurement sub-spaces and corresponding to the first, second to the $M^{th}$ photon energy levels are respectively represented as $I_{r1}(E_1)$, $I_{r1}(E_2)$ to $I_{r1}(E_M)$, the second intensities of the electromagnetic wave beam passing through each of the blocks and corresponding to the first, second to $M^{th}$ photon energy levels are respectively represented as $I_{r2}(E_1)$, $I_{r2}(E_2)$, to $I_{r2}(E_M)$, the proportion matrix is represented as $T_r$, and $$T_r = \begin{bmatrix} -\ln\left(\frac{I_{r2}(E_1)}{I_{r1}(E_1)}\right) \\ -\ln\left(\frac{I_{r2}(E_2)}{I_{r1}(E_2)}\right) \\ \vdots \\ -\ln\left(\frac{I_{r2}(E_M)}{I_{r1}(E_M)}\right) \end{bmatrix}$$

wherein the thickness of the substance having the first component, the thickness of the substance having the second component to the thickness of the substance having the $N^{th}$ component are respectively represented as $t_1$, $t_2$ to $t_N$, the first attenuation coefficients of each of the blocks respectively corresponding to the first, second to $N^{th}$ components irradiated by the electromagnetic wave beam corresponding to the first photon energy level are respectively represented as $\mu_{r1}(E_1)$, $\mu_{r1}(E_1)$ to $\mu_{rN}(E_1)$, and the processing unit calculates the first attenuation coefficients of each of the blocks respectively corresponding to the first, second to $N^{th}$ components irradiated by the electromagnetic wave beam corresponding to the first photon energy level by an equation (1):

$$\begin{bmatrix} \mu_{r1}(E_1) \cdot t_1 \\ \mu_{r2}(E_1) \cdot t_2 \\ \vdots \\ \mu_{rN}(E_1) \cdot t_N \end{bmatrix} = W^{-1} \cdot T_r. \quad (1)$$

12. The system as recited in claim 9, wherein the electromagnetic wave comprises a plurality of the electromagnetic wave beams respectively and simultaneously passing through the measurement sub-spaces, the electromagnetic wave detector has a plurality of sensing pixels corresponding to the measurement sub-spaces, the sensing pixels respectively and simultaneously measure the first intensities of the electromagnetic wave beams respectively passing through the measurement sub-spaces and corresponding to the photon energy levels, the electromagnetic wave beams respectively and simultaneously pass through the blocks, and the sensing pixels respectively and simultaneously measure the second intensities of the electromagnetic wave beams respectively passing through the blocks and corresponding to the photon energy levels.

13. The system as recited in claim 12, further comprising:
a control unit electrically connected to the electromagnetic wave providing unit and the electromagnetic wave detector, the control unit causing intensity of the electromagnetic wave beams emitted by the electromagnetic wave providing unit to be constant during a period of measuring the first intensity images and the second intensity images by the electromagnetic wave detector.

14. The system as recited in claim 12, further comprising:
a filter unit disposed on a transmission path of the electromagnetic wave beams and located between the electromagnetic wave providing unit and the measurement sub-spaces, the filter unit being configured to filter out part of the electromagnetic wave beams having photon energy less than a minimum of the photon energy levels.

15. The system as recited in claim 9, wherein the electromagnetic wave providing unit is a pulsed electromagnetic wave providing unit comprising a pulsed electromagnetic wave source and a collimator, the pulsed electromagnetic wave source provides a pulsed electromagnetic wave, the pulsed electromagnetic wave is the electromagnetic wave passing through the measurement space, the collimator is disposed on a transmission path of the pulsed electromagnetic wave and has a hole, a portion of the pulsed electromagnetic wave passes through the hole of the collimator and forms a pulsed electromagnetic wave beam, and the pulsed electromagnetic wave beam is the electromagnetic wave beam.

* * * * *